US009371483B2

(12) United States Patent
Junge

(10) Patent No.: US 9,371,483 B2
(45) Date of Patent: *Jun. 21, 2016

(54) SWITCH ELEMENT COMPRISING A LIQUID-CRYSTALLINE MEDIUM

(75) Inventor: Michael Junge, Pfungstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 91 days.

This patent is subject to a terminal disclaimer.

(21) Appl. No.: 13/702,669

(22) PCT Filed: May 12, 2011

(86) PCT No.: PCT/EP2011/002365
§ 371 (c)(1),
(2), (4) Date: Dec. 7, 2012

(87) PCT Pub. No.: WO2011/154077
PCT Pub. Date: Dec. 15, 2011

(65) Prior Publication Data
US 2013/0083284 A1 Apr. 4, 2013

Related U.S. Application Data

(60) Provisional application No. 61/354,952, filed on Jun. 15, 2010.

(30) Foreign Application Priority Data

Jun. 7, 2010 (GB) .................................. 1009488.6

(51) Int. Cl.
| | | |
|---|---|---|
| C09K 19/30 | (2006.01) |
| C09K 19/32 | (2006.01) |
| C09K 19/34 | (2006.01) |
| C09K 19/42 | (2006.01) |
| C07C 69/74 | (2006.01) |
| C07C 69/757 | (2006.01) |
| C07C 255/31 | (2006.01) |
| C07C 255/46 | (2006.01) |
| C07C 255/55 | (2006.01) |
| G02F 1/139 | (2006.01) |

(52) U.S. Cl.
CPC ............ *C09K 19/3098* (2013.01); *C07C 69/74* (2013.01); *C07C 69/757* (2013.01); *C07C 255/31* (2013.01); *C07C 255/46* (2013.01); *C07C 255/55* (2013.01); *C09K 19/3068* (2013.01); *C09K 19/321* (2013.01); *C09K 19/3402* (2013.01); *C09K 19/3452* (2013.01); *C09K 19/3455* (2013.01); *C09K 19/3458* (2013.01); *C09K 19/3475* (2013.01); *C09K 19/42* (2013.01); *G02F 1/139* (2013.01); *C09K 2019/3069* (2013.01); *C09K 2019/3071* (2013.01); *C09K 2019/3075* (2013.01); *C09K 2019/3077* (2013.01); *C09K 2219/13* (2013.01)

(58) Field of Classification Search
CPC ........... C09K 19/3068; C09K 19/3402; C09K 19/3452; C09K 19/3455; C09K 19/3458; C09K 19/3475; C09K 2019/3069; C09K 19/3098; C09K 19/321; C09K 2019/3071; C09K 2019/3075; C09K 2019/3077; C09K 2219/13; G02F 1/139
USPC ............ 428/1.1; 252/299.01, 299.61, 299.63, 252/299.66, 299.67; 349/196, 199
See application file for complete search history.

(56) References Cited

U.S. PATENT DOCUMENTS

| | | | |
|---|---|---|---|
| 4,261,652 A | 4/1981 | Gray et al. |
| 4,349,452 A | 9/1982 | Osman et al. |
| 4,400,061 A | 8/1983 | Carr et al. |
| 4,419,262 A | 12/1983 | Petrzilka |
| 4,421,105 A * | 12/1983 | Wilkinson et al. ............ 126/714 |
| 4,595,521 A | 6/1986 | Petrzilka et al. |
| 4,659,500 A | 4/1987 | Sugimori et al. |
| 4,824,596 A | 4/1989 | Kitano et al. |
| 5,030,384 A | 7/1991 | Fujimura |
| 6,781,664 B1 | 8/2004 | Heckmeier et al. |
| 6,793,983 B1 * | 9/2004 | Heckmeier ........ C09K 19/3001 252/299.61 |
| 2003/0224125 A1 | 12/2003 | Heckmeier et al. |
| 2004/0036058 A1 | 2/2004 | Heckmeier et al. |

(Continued)

FOREIGN PATENT DOCUMENTS

| | | |
|---|---|---|
| EP | 0 256 670 A2 | 2/1988 |
| EP | 0 309 870 A2 | 4/1989 |
| GB | 2 071 649 A | 9/1981 |
| GB | 2 079 275 A | 1/1982 |
| GB | 2 102 414 A | 2/1983 |
| GB | 2 162 515 A | 2/1986 |

OTHER PUBLICATIONS

International Search Report of PCT/EP2011/002365 (Oct. 10, 2011).
M. Osman et al., "Trans, Trans-Cyclohexyl Cyclohexanoates. A New Class of Aliphatic Liquid Crystals", Molecular Crystals and Liquid Crystals, vol. 56 (1979) pp. 105-109.
M. Petrzilka et al., "New Liquid Crystals: The Mesomorphic Properties of Mono- and Bisalkenyl(oxy) Substituted Esters", Molecular Crystals and Liquid Crystals, vol. 148 (1987) pp. 123-143.
N. Carr et al., "Some New Mesogenic Esters Incorporating the 1,4-Disubstituted Bicyclo(2.2.2) Octane Ring System", Molecular Crystals and Liquid Crystals, vol. 130 (1985) pp. 265-279.

*Primary Examiner* — Shean C Wu
(74) *Attorney, Agent, or Firm* — Millen, White, Zelano and Branigan, P.C.

(57) ABSTRACT

The present invention relates to a switch element, which is thermoresponsive and which switches between a less transmissive state for radiant energy and a more transmissive state for radiant energy, and which comprises a liquid-crystalline medium. The invention furthermore relates to the use of the switch element for the regulation of radiant energy flow between interior spaces and the environment and for the regulation of the temperature of interior spaces. The invention furthermore relates to a liquid-crystalline medium, characterized in that it comprises 5-60% of a compound of the formula (I), in particular for use in the switch elements according to the invention.

12 Claims, No Drawings

(56) References Cited

U.S. PATENT DOCUMENTS

| | | |
|---|---|---|
| 2009/0015902 A1 | 1/2009 | Powers et al. |
| 2009/0167971 A1 | 7/2009 | Powers et al. |
| 2009/0309066 A1 | 12/2009 | Klasen-Memmer et al. |
| 2010/0097563 A1 | 4/2010 | Zhang |
| 2013/0037746 A1* | 2/2013 | Junge ............... 252/299.61 |
| 2013/0087738 A1* | 4/2013 | Junge ............... 252/299.61 |
| 2013/0155338 A1* | 6/2013 | Junge ................... 349/20 |
| 2013/0208227 A1* | 8/2013 | Junge .................. 349/186 |

* cited by examiner

SWITCH ELEMENT COMPRISING A LIQUID-CRYSTALLINE MEDIUM

The present invention relates to a switch element, which is thermoresponsive and which switches between a less transmissive state for radiant energy and a more transmissive state for radiant energy, and which comprises a liquid-crystalline medium. The invention furthermore relates to the use of the switch element for the regulation of radiant energy flow between interior spaces and the environment and for the regulation of the temperature of interior spaces. The invention furthermore relates to a liquid-crystalline medium, characterised in that it comprises 5-60% of a compound of the formula (I), in particular for use in the switch element mentioned above.

The switch element is used in accordance with the invention in windows or comparable openings in buildings, such as, for example, in glazed doors, skylights and/or glass roofs for the regulation of light influx.

For the purposes of this invention, the term liquid-crystalline medium is to be taken to mean a material or compound which under certain conditions shows liquid-crystalline properties. Preferably, the liquid-crystalline medium shows thermotropic behavior, more preferably, the liquid-crystalline medium exhibits a temperature-induced phase transition from an isotropic to a liquid-crystalline phase, most preferably to a nematic phase.

For the purposes of this invention, the term interior space is intended to be taken to mean both interior spaces in private, public or commercial buildings, for example buildings used for office purposes, and also the interior spaces of vehicles. Furthermore, the term interior space is also intended to be taken to mean the interior spaces of buildings used purely commercially, such as, for example, greenhouses.

For the purposes of this invention, the term window is intended to be taken to mean any desired light-transmissive openings sealed by solid material in buildings, in transport containers or in vehicles.

For the purposes of this invention, radiant energy flow is taken to mean the flow of electromagnetic radiation which emanates from the sun, hits the earth after passing through the atmosphere and is only absorbed to a small extent, or not at all, by glass sheets. The electromagnetic radiation may alternatively also emanate from light sources other than the sun. Since relatively short-wavelength radiation (UV-B light) and long-wavelength infrared radiation are absorbed by the atmosphere or by glass sheets, for the purposes of this invention, the term "radiant energy" is understood to comprise UV-A light, light in the visible region (VIS light) and near-infrared (NIR) light.

The term light, unless defined more precisely, is likewise intended to be taken to mean electromagnetic radiation in the UV-A region, VIS region and near-infrared region.

According to commonly used definitions in the field of physical optics, for the purposes of this invention, UV-A-light is understood to be electromagnetic radiation of 320 to 380 nm wavelength. VIS-light is understood to be electromagnetic radiation of 380 to 780 nm wavelength. Near-infrared light (NIR) is understood to be electromagnetic radiation of 780 to 3000 nm wavelength. Therefore, for the purposes of this invention, the terms "radiant energy" and "light" are understood to be electromagnetic radiation of 320 to 3000 nm wavelength.

For the purposes of this invention, the term switch element thus denotes a device capable of switching between a state in which it has lower transmission for radiant energy and a state in which it has higher transmission for radiant energy, the term radiant energy being defined as above. The switch element may selectively switch in one or more sub-regions of the spectrum of radiant energy. The terms "device" and "switch element" are being used interchangeably in the following.

The switch element according to the invention is thermoresponsive. However, it may additionally also be controlled by one or more other mechanisms, for example by electrical current or mechanical mechanisms. Preferably, such other mechanisms are not present.

Modern buildings are distinguished by a high proportion of glass surfaces, which is desired both for aesthetic reasons and also in relation to the brightness and comfort of the interior spaces. It has become equally important in recent years that buildings used for living or commercial purposes and/or which are accessible to the public have high energy efficiency. This means that as little energy as possible has to be expended for heating purposes in the cold season in temperate climatic zones (where the majority of highly developed industrial nations are located) and no or only little air conditioning of the interior spaces is necessary in the warm season.

However, a high proportion of glass surfaces hinders the achievement of these aims. In warm climatic zones and in the warm season in temperate climatic zones, glass surfaces result in undesired heating of the interior spaces when they are hit by solar radiation. This is due to the fact that glass is transparent to radiation in the VIS and NIR region of the electromagnetic spectrum. Objects in the interior space absorb the radiation that is allowed through and are warmed thereby, which results in an increase in the temperature of the interior space (greenhouse effect).

This increase in temperature of the interior space behind a glass surface which is called greenhouse effect is due to the fact that the objects in the interior which have absorbed the radiation will also emit radiation. However, the emitted radiation of these objects is mainly in the infrared spectrum (typically about 10,000 nm wavelength) of light. It therefore cannot pass through the glass again and is "trapped" in the space behind the glazing.

However, the above-described effect of glass surfaces in buildings is not generally undesired: at low outside temperatures, in particular in cold climatic zones or in the cold season in temperate climatic zones, heating of the interior spaces owing to solar radiation due to the greenhouse effect may be advantageous since the energy requirement for heating is thereby reduced and costs can thus be saved.

With the increasing importance of energy efficiency of buildings, there is therefore a growing demand for devices which control the flow of energy through windows or glass surfaces. In particular, there is a demand for devices which enable the flow of energy through glass surfaces to be matched to the conditions (heat, cold, high solar radiation, low solar radiation) prevailing at the particular time.

Of particular interest is the provision of such devices in temperate climatic zones, in which a seasonal change occurs between warm outside temperatures combined with high solar radiation and cold outside temperatures combined with low solar radiation.

The prior art discloses both non-switchable devices, which limit the energy flow, but cannot be adapted in a variable manner, and also switchable devices, which are able to match the energy flow to the respective conditions prevailing. Amongst the switchable devices, a distinction should be made between devices which do not adapt automatically to the ambient conditions and devices which adapt automatically to the ambient conditions. The latter devices are also known as smart windows.

In order to improve the thermal insulation of windows, multiple-glazed window units (insulated glass units, IGU) have been known for some time. The sequence of two or more glass panes which enclose one or more gas-filled interspaces which are insulated from the environment enables thermal conduction through windows to be significantly reduced compared with single-glass panes. The prior art furthermore discloses the coating of glass surfaces with thin layers, e.g. metal or metal-oxide layers (U.S. Pat. No. 3,990,784 and U.S. Pat. No. 6,218,018).

If the radiant energy flow is controlled exclusively by a coating and/or by the use of insulating glass, however, adaptation to varying weather or seasonal conditions is not possible. For example, it would be of interest for windows to be totally transparent to sunlight at cold outside temperatures in order to reduce the energy consumption for heating. Conversely, it would be desirable for windows to allow less sunlight to pass through at warm outside temperatures, so that less heating of the interior spaces takes place.

There is therefore a demand for devices in which the radiant energy flow can be matched to the respective conditions prevailing. In particular, there is a demand for devices which are able to adapt automatically to the ambient conditions.

The prior art furthermore discloses devices which, on application of an electrical voltage, can be switched reversibly from a light-transmissive state to a less light-transmissive state. The first state will also be referred to as bright state in the following, whereas the second state will be referred to as dark state.

A possible embodiment of electrically switchable devices are electro-chromic devices, which are presented, inter alia, in Seeboth et al., Solar Energy Materials & Solar Cells, 2000, 263-277. A further review is offered by C. M. Lampert et al., Solar Energy Materials & Solar Cells, 2003, 489-499.

Further electrically switchable devices known from the prior art are based on the alignment of molecules of a liquid-crystalline medium on application of an electric field. Such devices are disclosed, inter alia, in U.S. Pat. No. 4,268,126, U.S. Pat. No. 4,641,922, U.S. Pat. No. 5,940,150 and WO 2008/027031 and likewise switch under electrical control from a bright state to a dark transparent state.

Although the electrically switchable devices mentioned above enable the radiant energy flow to be set, they have the disadvantage of having to be electrically controlled.

It would be desirable to have available a switch element which adapts automatically to the ambient conditions and which does not have to be controlled either manually or by any additional coupled device capable of giving a signal upon a detected temperature deviation.

It would furthermore be desirable to have available a switch element which does not require any electrical circuits. The introduction of electrical circuits into windows is accompanied by additional work during manufacture of the windows and entails the risk of susceptibility to flaws or a short service life of the devices. Furthermore, additional infrastructure is necessary for such devices, including electrical power supply.

Devices which are not electrically switched, but instead are, for example, temperature-controlled (thermoresponsive devices), are described, inter alia, in Nitz et al., Solar Energy 79, 2005, 573-582. A possible embodiment of such devices are systems which are based on the separation between two phases above a certain temperature. Further embodiments are based on temperature-dependent properties of hydrogels. However, these devices typically switch between a transparent state and a dark translucent (scattering) state, which is undesired for applications in which it is required that the device stays transparent also in the dark state.

US 2009/0015902 and US 2009/0167971 disclose optical switch elements comprising a liquid-crystalline medium between two polarisers. The liquid-crystalline medium has the property of rotating the plane of polarisation of the light at a first temperature and not rotating or essentially not rotating the plane of polarisation of the light at a second temperature. Thus, a suitable arrangement of the polarisers enables the devices to allow more light to pass through at the first temperature than at the second temperature. The two temperature-dependent states represent a bright state (first temperature) and a dark transparent state (second temperature), and are preferably caused by a change of the liquid-crystalline medium from a nematic state (first temperature, liquid-crystalline medium is rotating the plane of polarisation of light) to an isotropic state (second temperature, liquid-crystalline medium is not rotating the plane of polarisation of light).

The applications US 2009/0015902 and US 2009/0167971 furthermore disclose that liquid-crystalline media having a low clearing point are suitable for use in the said devices. The switching process from the bright state to the dark transparent state, which is caused by the phase transition of the liquid-crystalline medium, is intended to take place merely on heating of the device by the typical radiation intensity of the sun in the warm season. To this end, a preferred clearing point of below 85° C. is disclosed. An example disclosed is a liquid-crystalline medium which comprises the liquid-crystalline mixture E7 together with added 4'-hexyl-4-cyanobiphenyl (6CB) and which has a clearing point of 35° C. It is furthermore generally disclosed in the above-mentioned applications that the liquid-crystalline mixture ZL11132 (Merck KGaA) with a clearing point of 72° C. can alternatively also be used as the basis for the preparation of liquid-crystalline media for use in the switchable devices. However, no specific illustrative embodiments are disclosed in this respect.

In this respect, it is to be noted that the modification of mixture E7 disclosed in US 2009/0015902 and US 2009/0167971 by addition of alkylcyanobiphenyl compounds, such as, for example, 4'-hexyl-4-cyanobiphenyl, has the disadvantage that the low-temperature stability of the liquid-crystalline medium is impaired.

A good low-temperature stability of the liquid-crystalline medium is however highly desirable, since in many applications, the switch element is exposed to low temperatures for extended periods of time.

There continues to be a demand for liquid-crystalline media which are suitable for use in thermally switchable devices. In particular, there is a demand for liquid-crystalline media which have a transition from a nematic state to an isotropic state (clearing point) at a temperature which is within the operating-temperature range of the switch element. There is furthermore a demand for liquid-crystalline media which have a high content of cycloaliphatic two-ring compounds, since such two-ring compounds can be prepared cost-effectively. There is furthermore a demand for liquid-crystalline media which have good low-temperature storage stability, preferably in combination with the properties mentioned above.

To this end, the present invention provides a switch element, characterised in that it is thermoresponsive and that it switches between a less transmissive state for radiant energy and a more transmissive state for radiant energy, comprising a liquid-crystalline medium, which comprises one or more compounds of the formula (I)

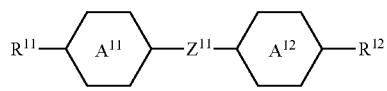
formula (I)

where
$R^{11}$, $R^{12}$ are on each occurrence, identically or differently, selected from F, Cl, CN, NCS, $R^1$—O—CO—, $R^1$—CO—O—, an alkyl, alkoxy or thioalkoxy group having 1 to 10 C atoms and an alkenyl, alkenyloxy or thioalkenyloxy group having 2 to 10 C atoms, where one or more H atoms in the groups mentioned above may be replaced by F or Cl, and where one or more $CH_2$ groups in the groups mentioned above may be replaced by O, S, —O—CO— or —CO—O—; and where
$R^1$ is, identically or differently on each occurrence, an alkyl or an alkenyl group having 1 to 10 C atoms, in which one or more H atoms may be replaced by F or Cl; and

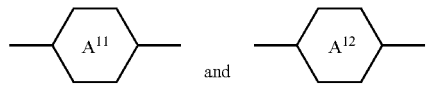

are selected from

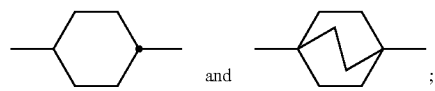

and
$Z^{11}$ is selected from —CO—O— and —O—CO—.

Preferentially, the liquid-crystalline medium furthermore comprises one or more compounds of the formula (II)

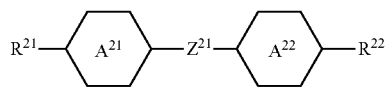
formula (II)

where
$R^{21}$, $R^{22}$ have the meanings indicated for $R^{11}$ and $R^{12}$ above; and

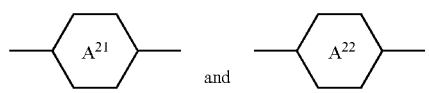

are selected from

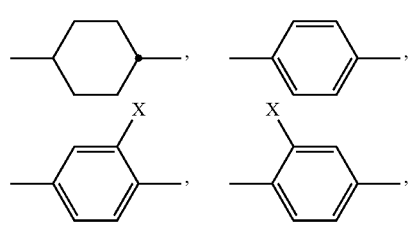

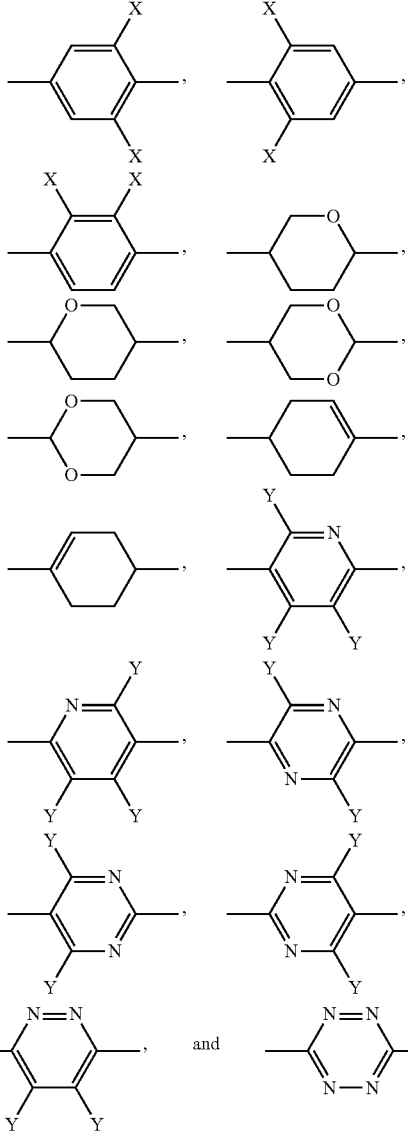

and
X is on each occurrence, identically or differently, F, Cl, CN or an alkyl, alkoxy or thioalkoxy group having 1 to 10 C atoms, where one or more H atoms in the groups mentioned above may be replaced by F or Cl and where one or more $CH_2$ groups may be replaced by O or S; and
Y is on each occurrence, identically or differently, selected from H and X; and
$Z^{21}$ is selected from —CO—O—, —O—CO—, —$CF_2$O—, —O$CF_2$—, —$CH_2CH_2$—, —O$CH_2$—, —$CH_2$O— and a single bond;
with the proviso that if

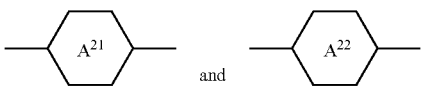

are both selected to be

, $Z^{21}$ must not be —CO—O— or —O—CO—.

Preferentially, the liquid-crystalline medium furthermore comprises one or more compounds selected from compounds of the formulas (III) and (IV)

formula (III)

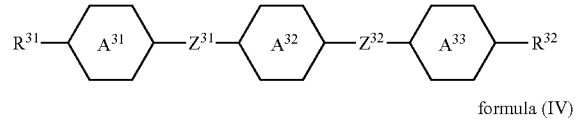

formula (IV)

where $R^{31}$, $R^{32}$, $R^{41}$ and $R^{42}$ have the meanings indicated for $R^{11}$ and $R^{12}$ above; and

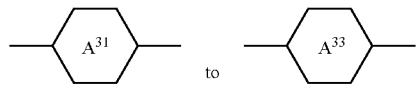

are on each occurrence, identically or differently, selected from

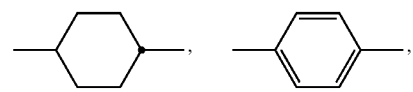

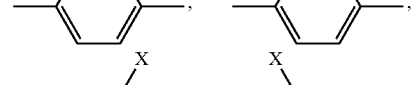

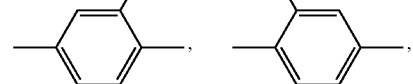

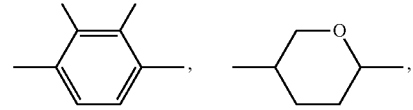

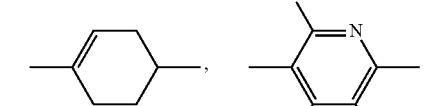

,

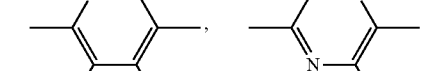

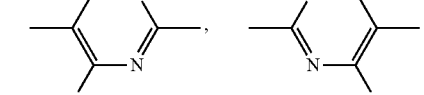

and

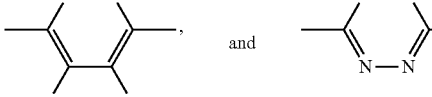

;

where X and Y are defined as above; and

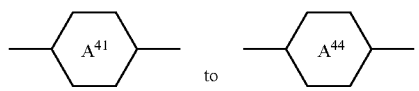

are on each occurrence, identically or differently, selected from

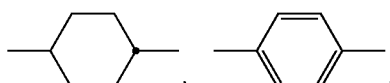

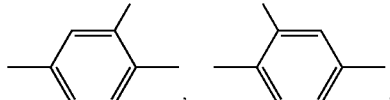

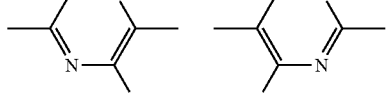

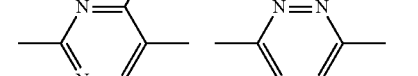

, and

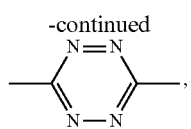

where X and Y are defined as above; and $Z^{31}$ and $Z^{32}$ are on each occurrence, identically or differently, selected from —CO—O—, —O—CO—, —CF$_2$O—, —OCF$_2$—, —CH$_2$CH$_2$—, —OCH$_2$—, —CH$_2$O— and a single bond; and $Z^{41}$, $Z^{42}$ and Z43 are on each occurrence, identically or differently, selected from —CO—O—, —O—CO— and a single bond.

According to a preferred embodiment of the invention, the liquid-crystalline medium comprises one or more compounds of formula (I) and one or more compounds of formula (II) and one or more compounds selected from compounds of the formulas (III) and (IV), as defined above.

According to a preferred embodiment of the invention, X is, identically or differently on each occurrence, selected from F, Cl, CN and an alkyl or alkoxy group having 1 to 8 C atoms. It is particularly preferred that X is selected from F and Cl, and it is very particularly preferred that X is F.

Furthermore, it is preferred that $R^{11}$ and $R^{12}$ are on each occurrence, identically or differently, selected from F, Cl, CN, $R^1$—O—CO—, $R^1$—CO—O—, a straight-chain alkyl or alkoxy group having 1 to 10 C atoms and an alkenyl or alkenyloxy group having 2 to 10 C atoms, where one or more H atoms in the groups mentioned above may be replaced by F or Cl, and where one or more CH$_2$ groups in the groups mentioned above may be replaced by —O—CO—, —CO—O—, $R^1$ being defined as above.

For compounds according to formula (I), it is preferred that $R^{11}$ is selected from $R^1$—O—CO—, $R^1$—CO—O— and a straight-chain alkyl or alkoxy group having 1 to 10 C atoms, where one or more H atoms in the groups mentioned above may be replaced by F or Cl and where one or more CH$_2$ groups in the groups mentioned above may be replaced by —O—CO— or —CO—O—, $R^1$ being defined as above.

For compounds according to formula (I), it is furthermore preferred that $Z^{11}$ is —CO—O—.

According to a particularly preferred embodiment of the invention, compounds according to formula (I) are compounds of the following formulas (I-1) to (I-4):

formula (I-1)
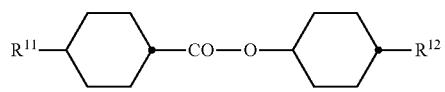

formula (I-2)
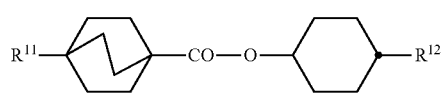

formula (I-3)
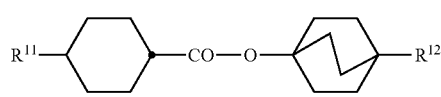

formula (I-4)
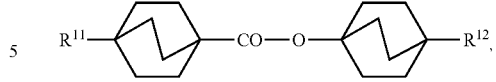

where $R^{11}$ and $R^{12}$ are defined as above.

According to an even more preferred embodiment, compounds according to formula (I-1) are compounds of the following formulas (I-1a) to (I-1c)

formula (I-1a)
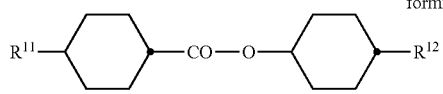

formula (I-1b)
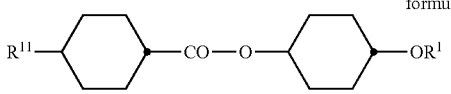

formula (I-1c)
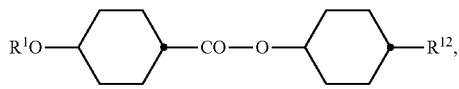

where $R^{11}$ and $R^{12}$ are, identically or differently on each occurrence, an alkyl group having 1 to 10 C atoms, where one or more CH$_2$ groups may be replaced by —O—CO— or —CO—O—, and $R^1$ is an alkyl group having 1 to 10 C atoms.

According to a further even more preferred embodiment, compounds according to formula (I-2) are compounds of the following formulas (I-2a) to (I-2c)

formula (I-2a)
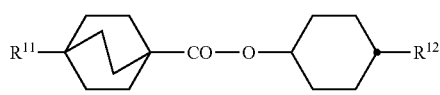

formula (I-2b)
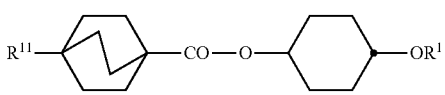

formula (I-2c)
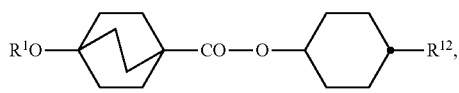

where $R^{11}$ and $R^{12}$ are, identically or differently on each occurrence, an alkyl group having 1 to 10 C atoms, where one or more CH$_2$ groups may be replaced by —O—CO— or —CO—O—, and $R^1$ is an alkyl group having 1 to 10 C atoms.

According to a further even more preferred embodiment, compounds according to formula (I-3) are compounds of the following formulas (I-3a) to (I-3c)

formula (I-3a)

$R^{11}$—⟨cyclohexyl⟩—CO—O—⟨bicyclo⟩—$R^{12}$ formula (I-3b)

$R^{11}$—⟨cyclohexyl⟩—CO—O—⟨bicyclo⟩—$OR^1$ formula (I-3c)

$R^1O$—⟨cyclohexyl⟩—CO—O—⟨bicyclo⟩—$R^{12}$, where $R^{11}$ and $R^{12}$ are, identically or differently on each occurrence, an alkyl group having 1 to 10 C atoms, where one or more $CH_2$ groups may be replaced by —O—CO— or —CO—O—, and
$R^1$ is an alkyl group having 1 to 10 C atoms.

According to a further even more preferred embodiment, compounds according to formula (I-4) are compounds of the following formulas (I-4a) to (I-4c)

formula (I-4a)

$R^{11}$—⟨bicyclo⟩—CO—O—⟨bicyclo⟩—$R^{12}$ formula (I-4b)

$R^{11}$—⟨bicyclo⟩—CO—O—⟨bicyclo⟩—$OR^1$ formula (I-4c)

$R^1O$—⟨bicyclo⟩—CO—O—⟨bicyclo⟩—$R^{12}$, where $R^{11}$ and $R^{12}$ are, identically or differently on each occurrence, an alkyl group having 1 to 10 C atoms, where one or more $CH_2$ groups may be replaced by —O—CO— or —CO—O—, and
$R^1$ is an alkyl group having 1 to 10 C atoms.

According to a most preferred embodiment, compounds according to formula (I) are compounds of the formulas (I-1a) to (I-1c).

According to a preferred embodiment, in compounds according to formula (II), $A^{21}$ is selected from ⟨cyclohexyl⟩, ⟨phenyl⟩ and ⟨dioxane⟩;

and

—⟨$A^{22}$⟩— is selected from

⟨cyclohexyl⟩, ⟨phenyl⟩,

⟨phenyl with X⟩, ⟨phenyl with X⟩,

⟨phenyl with X,X⟩, ⟨phenyl with X,X⟩ and

⟨phenyl with X,X⟩;

where X is defined as above.

According to a further preferred embodiment, $Z^{21}$ is —CO—O—, —$CH_2CH_2$— or a single bond.

According to a further preferred embodiment, $R^{21}$ and $R^{22}$ are, identically or differently on each occurrence, F, Cl, CN or an alkyl or alkoxy group having 1 to 10 C atoms, in which one or more H atoms may be replaced by F or Cl or an alkenyl group having 2 to 10 C atoms.

According to a particularly preferred embodiment, compounds according to formula (II) are compounds of the following formulas (II-1) to (II-3)

formula (II-1)

$R^{21}$—⟨$A^{21}$⟩—CO—O—⟨$A^{22}$⟩—$R^{22}$ formula (II-2)

$R^{21}$—⟨$A^{21}$⟩—$CH_2$—$CH_2$—⟨$A^{22}$⟩—$R^{22}$ formula (II-3)

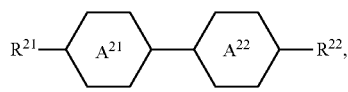

where $R^{21}$, $R^{22}$,

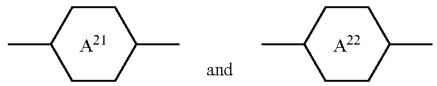

are defined as above, with the proviso that for formula (II-1), the case is excluded where

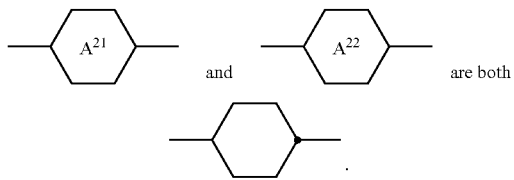
are both

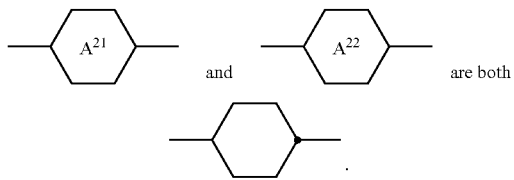.

According to a preferred embodiment, in compounds according to formula (II-1),

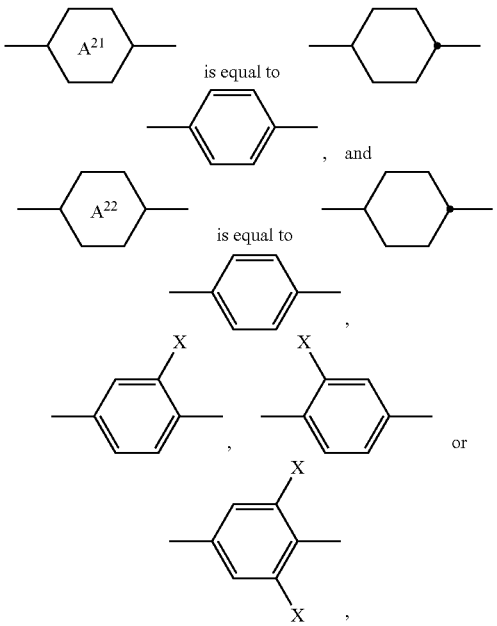

where
X is defined as above, with the proviso that the case is excluded where

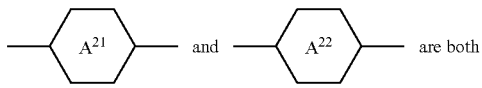
are both

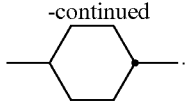.

According to a further preferred embodiment, in compounds according to formula (II-2),

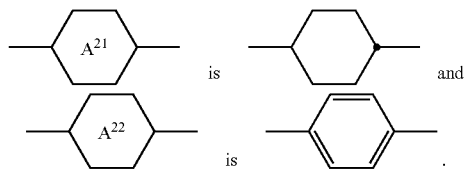

According to a further preferred embodiment, in compounds according to formula (II-3),

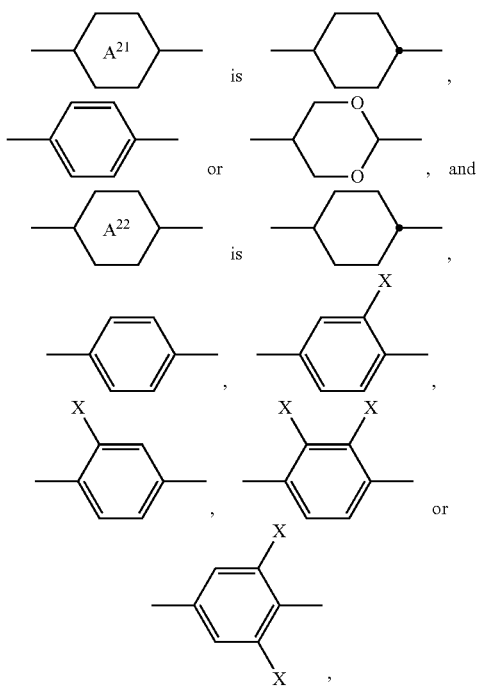

where X is defined as above.

Particularly preferred embodiments of compounds according to formula (II-1) are compounds of the following formulas (II-1a) to (II-1e)

formula (II-1a)

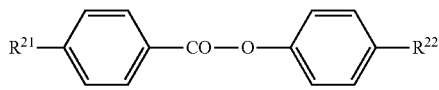

formula (II-1b)

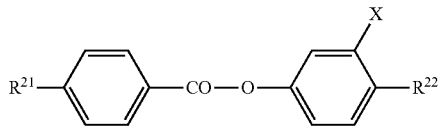

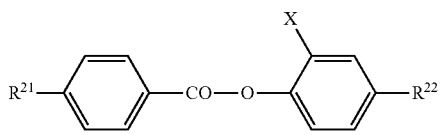
formula (II-1c)

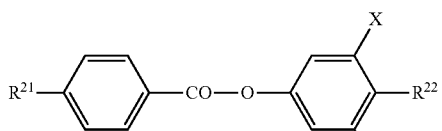
formula (II-1d)

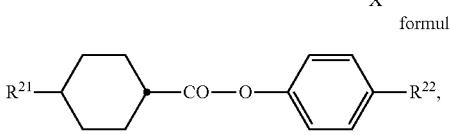
formula (II-1e)

where $R^{21}$, $R^{22}$ and X are defined as above.

Particularly preferred embodiments of compounds according to formula (II-2) are compounds of the following formula (II-2a)

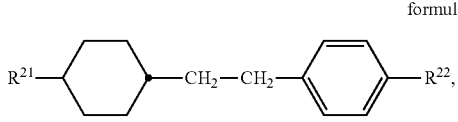
formula (II-2a)

where $R^{21}$ and $R^{22}$ are defined as above.

Particularly preferred embodiments of compounds according to formula (II-3) are compounds of the following formulas (II-3a) to (II-3h)

formula (II-3a)

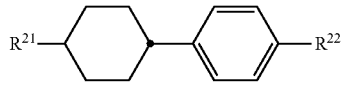
formula (II-3b)

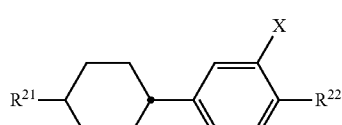
formula (II-3c)

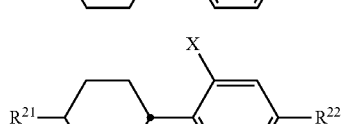
formula (II-3d)

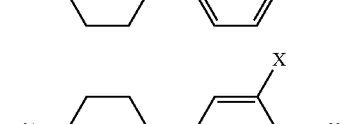
formula (II-3e)

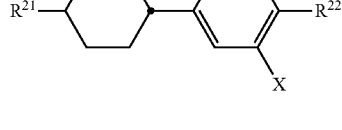
formula (II-3f)

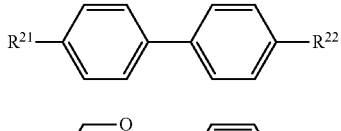
formula (II-3f)

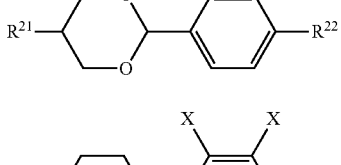
formula (II-3g)

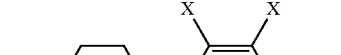
formula (II-3h)

where $R^{21}$, $R^{22}$ and X are defined as above.

Most preferred embodiments of compounds according to formula (II-1a) are compounds of the following formulas (II-1a-1) to (II-1a-3)

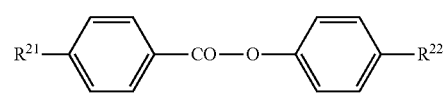
formula (II-1a-1)

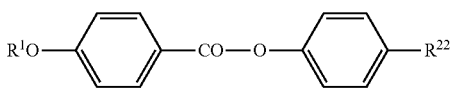
formula (II-1a-2)

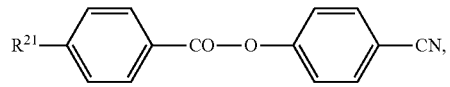
formula (II-1a-3)

where $R^1$, $R^{21}$ and $R^{22}$ are defined as above.

Preferably, in compounds according to formulas (II-1a-1) to (II-1a-3), $R^1$, $R^{21}$ and $R^{22}$ are selected from alkyl groups having 1 to 10 C atoms.

Most preferred embodiments of compounds according to formula (II-1b) are compounds of the following formula (II-1b-1)

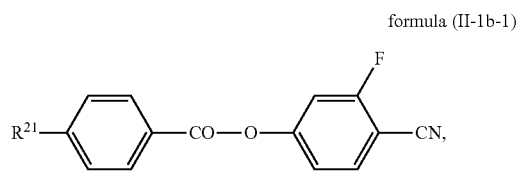
formula (II-1b-1)

where $R^{21}$ is defined as above.

Preferably, in compounds according to formula (II-1 b-1), $R^{21}$ is an alkyl group having 1 to 10 C atoms.

Most preferred embodiments of compounds according to formula (II-1e) are compounds of the following formula (II-1e-1)

formula (II-1e-1)

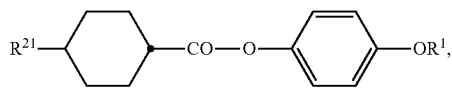

where $R^1$ and $R^{21}$ are defined as above.

Preferably, in compounds according to formula (II-1e-1), $R^1$ and $R^{21}$ are selected from alkyl groups having 1 to 10 C atoms.

Most preferred embodiments of compounds according to formula (II-2a) are compounds of the following formula (II-2a-1)

(formula (II-2a-1))

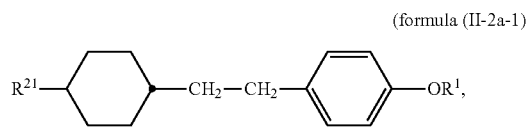

where $R^1$ and $R^{21}$ are defined as above.

Preferably, in compounds according to formula (II-2a-1), $R^1$ and $R^{21}$ are selected from alkyl groups having 1 to 10 C atoms.

Most preferred embodiments of compounds according to formula (II-3a) are compounds of the following formulas (II-3a-1) to (II-3a-2)

formula (II-3a-1)

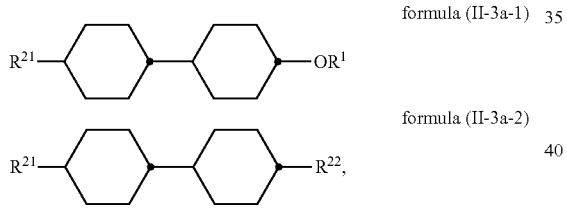

formula (II-3a-2)

where $R^1$, $R^{21}$ and $R^{22}$ are defined as above.

Preferably, in compounds according to formula (II-3a-1), $R^1$ and $R^{21}$ are selected from alkyl groups having 1 to 10 C atoms. Preferably, in compounds according to formula (II-3a-2), $R^{21}$ is selected from an alkyl group having 1 to 10 C atoms and $R^{22}$ is selected from an alkenyl group having 1 to 10 C atoms.

Most preferred embodiments of compounds according to formula (II-3b) are compounds of the following formulas (II-3b-1) to (II-3b-3)

formula (II-3b-1)

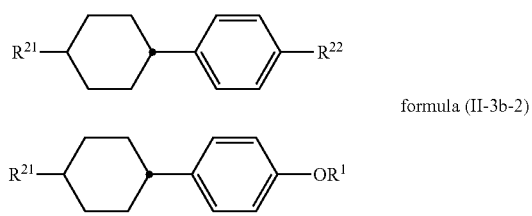

formula (II-3b-2)

formula (II-3b-3)

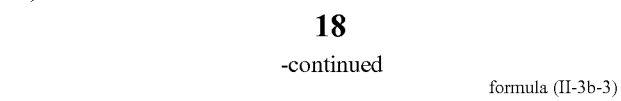

where $R^1$, $R^{21}$ and $R^{22}$ are defined as above.

Preferably, in compounds according to formulas (II-3b-1) to (II-3b-3), $R^1$, $R^{21}$ and $R^{22}$ are selected from alkyl groups having 1 to 10 C atoms.

Most preferred embodiments of compounds according to formula (II-3e) are compounds of the following formula (II-3e-1)

formula (II-3e-1)

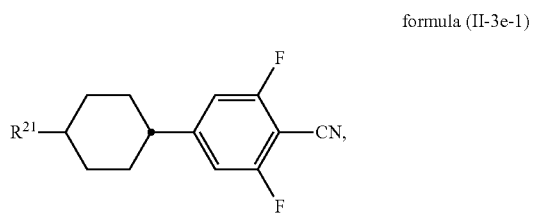

where $R^{21}$ is defined as above.

Preferably, in compounds according to formula (II-3e-1), $R^{21}$ is selected from alkyl groups having 1 to 10 C atoms.

Most preferred embodiments of compounds according to formula (II-3f) are compounds of the following formula (II-3f-1)

formula (II-3f-1)

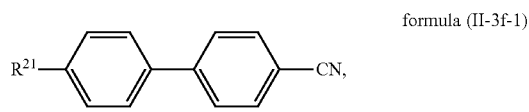

where $R^{21}$ is defined as above.

Preferably, in compounds according to formula (II-3f-1), $R^{21}$ is selected from alkyl groups having 1 to 10 C atoms.

Most preferred embodiments of compounds according to formula (II-3h) are compounds of the following formula (II-3h-1)

formula (II-3h-1)

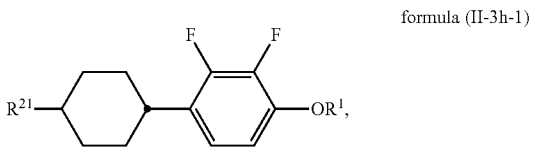

where $R^1$ and $R^{21}$ are defined as above.

Preferably, in compounds according to formula (II-3h-1), $R^1$ and $R^{21}$ are selected from alkyl groups having 1 to 10 C atoms.

According to a further preferred embodiment, in compounds according to formula (III),

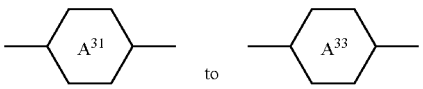 to are on each occurrence, identically or differently, selected from

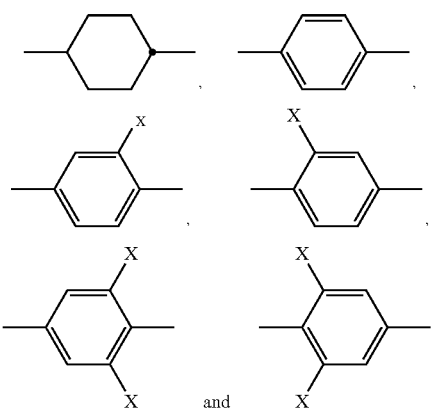

where X is defined as above.

According to a further preferred embodiment, in compounds according to formula (III), $Z^{31}$ and $Z^{32}$ are, identically or differently on each occurrence, —CO—O—, —O—CO—, —CH$_2$—CH$_2$— or a single bond.

According to a further preferred embodiment, in compounds according to formula (III), $R^{21}$ and $R^{22}$ are, identically or differently on each occurrence, F, Cl or CN or an alkyl group having 1 to 10 C atoms, in which one or more H atoms may be replaced by F or Cl.

According to a particularly preferred embodiment, compounds according to formula (III) are compounds of the following formulas (III-1) to (III-3)

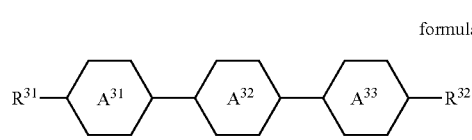

formula (III-1)

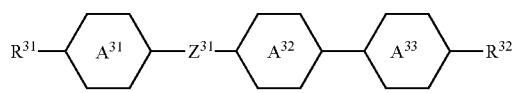

formula (III-2)

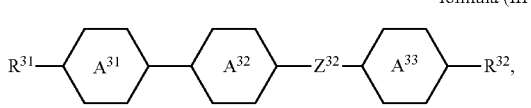

formula (III-3)

where the groups $R^{31}$, $R^{32}$, $Z^{31}$, $Z^{32}$ and

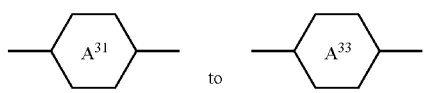

are defined as above.

According to a preferred embodiment, in compounds according to formula (III-1),

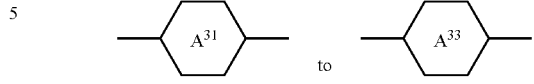

are on each occurrence, identically or differently, selected from

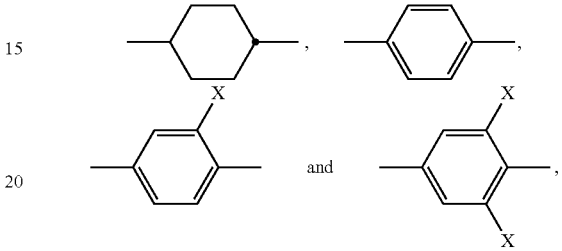

where
X is defined as above.

According to a further preferred embodiment, in compounds according to formula (III-2),

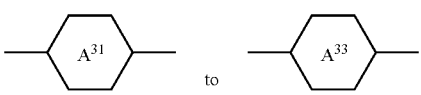

are on each occurrence, identically or differently, selected from

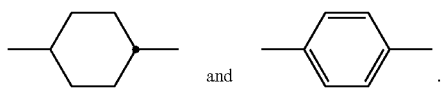

According to a further preferred embodiment, in compounds according to formula (III-3),

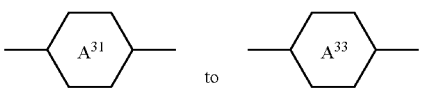

are on each occurrence, identically or differently, selected from

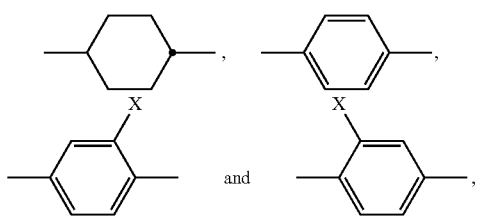

where

X is defined as above.

According to a particularly preferred embodiment of the invention, compounds of the formula (III-1) are compounds of the following formulas (III-1a) to (III-1e)

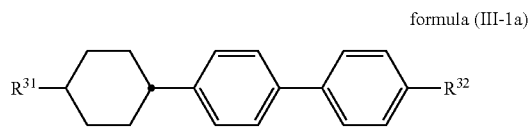
formula (III-1a)

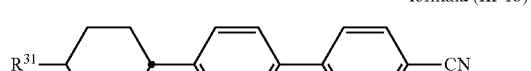
formula (III-1b)

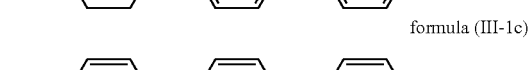
formula (III-1c)

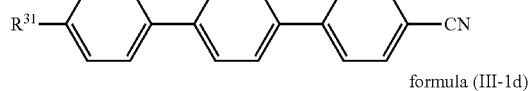
formula (III-1d)

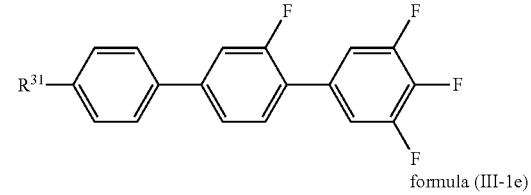
formula (III-1e)

where $R^{31}$ and $R^{32}$ are defined as above.

According to a particularly preferred embodiment of the invention, in compounds according to formulas (III-1a) to (III-1e), $R^{31}$ and $R^{32}$ are, identically or differently on each occurrence, selected from alkyl groups having 1 to 10 C atoms.

According to a further particularly preferred embodiment of the invention, compounds of the formula (III-2) are compounds of the following formulas (III-2a) to (III-2b)

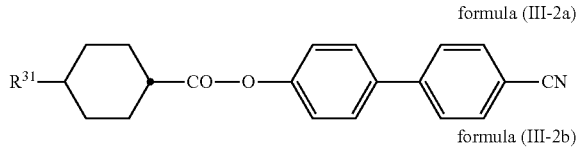
formula (III-2a)

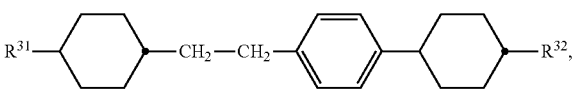
formula (III-2b)

where $R^{31}$ and $R^{32}$ are defined as above.

According to a particularly preferred embodiment of the invention, in compounds according to formulas (III-2a) and (III-2b), $R^{31}$ and $R^{32}$ are selected from alkyl groups having 1 to 10 C atoms.

According to a further particularly preferred embodiment of the invention, compounds of the formula (III-3) are compounds of the following formulas (III-3a) to (III-3c)

formula (III-3a)

formula (III-3b)

formula (III-3c)

where

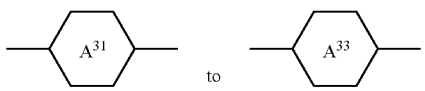

are on each occurrence, identically or differently, selected from

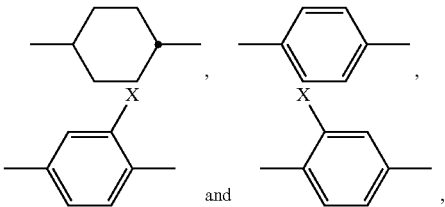

where

X is defined as above, and $R^{31}$ and $R^{32}$ are defined as above.

According to a most preferred embodiment of the invention, compounds of the formula (III-3a) are compounds of the following formulas (III-3a-1) to (III-3a-6)

formula (III-3a-1)

formula (III-3a-2)

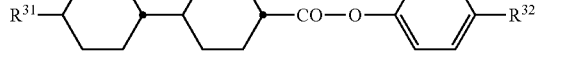
formula (III-3a-3)

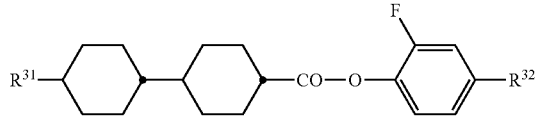

-continued

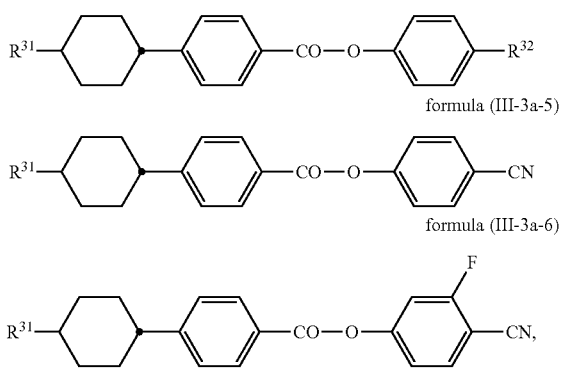

where $R^{31}$ and $R^{32}$ are defined as above.

Preferably, in compounds according to formulas (III-3a-1) to (III-3a-6), $R^{31}$ and $R^{32}$ are, identically or differently on each occurrence, selected from alkyl groups having 1 to 10 C atoms.

According to a further most preferred embodiment of the invention, compounds of the formula (III-3b) are compounds of the following formula (III-3b-1)

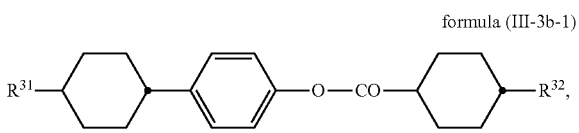

where $R^{31}$ and $R^{32}$ are defined as above.

Preferably, in compounds according to formula (III-3b-1), $R^{31}$ and $R^{32}$ are, identically or differently on each occurrence, selected from alkyl groups having 1 to 10 C atoms.

According to a further most preferred embodiment of the invention, compounds of the formula (III-3c) are compounds of the following formulas (III-3c-1) to (III-3c-3)

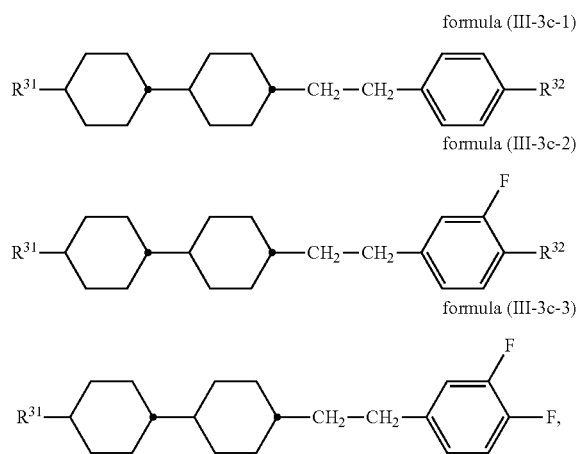

where $R^{31}$ and $R^{32}$ are defined as above.

Preferably, in compounds according to formula (III-3c-1) to (III-3c-3), $R^{31}$ and $R^{32}$ are, identically or differently on each occurrence, selected from alkyl groups having 1 to 10 C atoms, in which one or more H atoms may be replaced by F or Cl.

According to a further preferred embodiment, in compounds according to formula (IV),

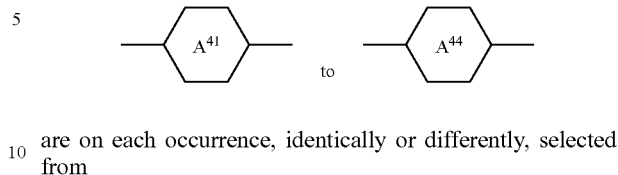

are on each occurrence, identically or differently, selected from

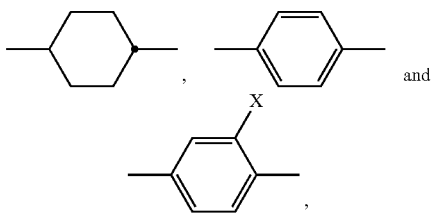

where
X is defined as above.

According to a further preferred embodiment, in compounds according to formula (IV),
$Z^{41}$ to $Z^{43}$ are, identically or differently on each occurrence, —CO—O— or a single bond.

According to a further preferred embodiment, in compounds according to formula (IV),
$R^{41}$ and $R^{42}$ are, identically or differently on each occurrence, an alkyl group having 1 to 10 C atoms.

According to a preferred embodiment of the invention, compounds according to formula (IV) are compounds of the following formulas (IV-1) and (IV-2)

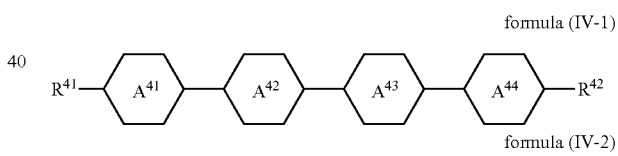

where $R^{41}$ and $R^{42}$ and

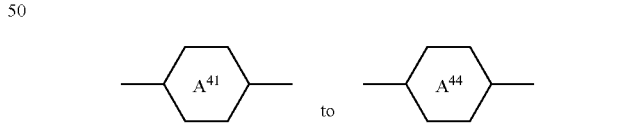

are defined as above.

According to a particularly preferred embodiment of the invention, compounds according to formula (IV-1) are compounds of the following formulas (IV-1a) to (IV-1 b)

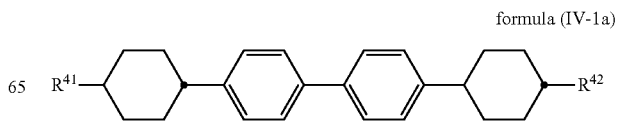

-continued

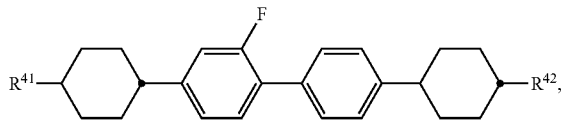
formula (IV-1b)

where $R^{41}$ and $R^{42}$ are defined as above.

According to a preferred embodiment, $R^{41}$ and $R^{42}$ in formulas (IV-1a) to (IV-1 b) are, identically or differently on each occurrence, an alkyl group having 1 to 10 C atoms.

According to a further particularly preferred embodiment of the invention, compounds according to formula (IV-2) are compounds of the following formula (IV-2a)

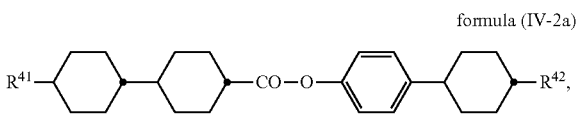
formula (IV-2a)

where $R^{41}$ and $R^{42}$ are defined as above.

According to a preferred embodiment, $R^{41}$ and $R^{42}$ in formula (IV-2a) are, identically or differently on each occurrence, an alkyl group having 1 to 10 C atoms.

According to a preferred embodiment of the invention, the total concentration of the compounds of the formula (I) is between 5 and 60%. More preferably, the concentration of the compounds according to formula (I) is between 5 and 40%, most preferably between 5 and 30%.

It is furthermore preferred that the total concentration of the compounds of formula (II) is between 1 and 90%. More preferably, the concentration of the compounds according to formula (II) is between 20 and 90%, most preferably between 40 and 85%.

It is furthermore preferred that the total concentration of the compounds of the formulas (I) and (II) is between 40 and 100%. More preferably, the concentration of the compounds according to formulas (I) and (II) is between 45 and 100%, most preferably between 50 and 100%.

It is furthermore preferred that the total concentration of the compounds of the formulas (III) and (IV) is between 0 and 45%.

The invention concerns furthermore a liquid-crystalline medium comprising one or more compounds of the formula (I) as defined above in a total concentration of 5 to 60% and at least one further compound of the formula (II) as defined above, so that the total concentration of the compounds of the formulas (I) and (II) is between 40 and 100%.

According to a preferred embodiment of the invention, the liquid-crystalline medium comprises at least 5 different compounds selected from the compounds of formulas (I) to (IV). According to a particularly preferred embodiment, the liquid-crystalline medium comprises at least 6 different compounds selected from the compounds of formulas (I) to (IV). According to an even more preferred embodiment, the liquid-crystalline medium comprises at least 7 different compounds selected from the compounds of formulas (I) to (IV).

Optionally the media according to the present invention may comprise further liquid crystal compounds in order to adjust the physical properties. Such compounds are known to the expert. Their concentration in the media according to the instant invention is preferably 0% to 30%, more preferably 0.1% to 20% and most preferably 1% to 15%.

The liquid crystal media according to the present invention may contain chiral dopants as further additives in usual concentrations. Preferred chiral dopants are listed in Table E below. The total concentration of these further constituents is in the range of 0% to 10%, preferably 0.1% to 6%, based on the total mixture. The concentrations of the individual compounds used each are preferably in the range of 0.1% to 3%. The concentration of these and of similar additives is not taken into consideration for the values and ranges of the concentrations of the liquid crystal components and compounds of the liquid crystal media in this application.

The liquid crystalline media according to the present invention may contain dyes as further additives in usual concentrations. In a preferred embodiment, dyes or combinations of dyes leading to grey or black color are used. In a further preferred embodiment, the dyes are selected from dyes with high light stability and good solubility, e.g. azo-dyes or anthraquinone dyes. The total concentration of these further constituents is in the range of 0% to 10%, preferably 0.1% to 6%, based on the total mixture. The concentrations of the individual compounds used each are preferably in the range of 0.1% to 9%. The concentrations of these and of similar additives is not taken into consideration for the values and ranges of the concentrations of the liquid crystal components and compounds of the liquid crystal media in this application.

The liquid crystalline media according to the invention may contain stabilizers as further additives in usual concentrations. Preferred stabilizers are listed in Table F below. The total concentration of the stabilizers is in the range of 0% to 10%, preferably 0.0001% to 1%, based on the total mixture.

According to a preferred embodiment of the invention, the clearing point (the temperature of the phase transition from the nematic to the isotropic state, T(N,I)) is lower than 60° C. According to a particularly preferred embodiment, T(N,I) is lower than 50° C. According to an even more preferred embodiment, T(N,I) is lower than 40° C.

A preferred liquid-crystalline medium for use in the switch element according to the invention comprises (liquid-crystalline medium I)
  one or more compounds according to formulas (I-1a) to (I-1c), (I-2a) to (I-2c), (I-3a) to (I-3c) and (I-4a) to (I-4c) in a total concentration of 5 to 60%,
  one or more compounds according to formula (II-3f) in a total concentration of 1 to 40%,
  one or more compounds according to formulas (II-1a) to (II-1e), (II-2a), (II-3a) to (II-3e) and (II-3g) and (II-3h) in a total concentration of 0 to 80%, and
  one or more compounds according to formulas (III-1a) to (III-1e), (III-2a) to (III-2b), (III-3a) to (III-3c), (IV-1a), (IV-1b) and (IV-2a) in a total concentration of 0 to 45%,
where the total concentration of the compounds of the formulas (I) and (II) is between 40 and 100%.

A more preferred liquid-crystalline medium for use in the switch element according to the invention comprises (preferred liquid-crystalline medium I)
  one or more compounds according to formulas (I-1a) to (I-1c) in a total concentration of 5 to 60%,
  one or more compounds according to formula (II-3f-1) in a total concentration of 1 to 40%,
  one or more compounds according to formulas (II-1a-1) to (II-1a-3), (II-1b-1), (II-1e-1), (II-2a-1), (II-3a-1) to (II-3a-2), (II-3b-1) to (II-3b-3) and (II-3e-1) and (II-3h-1) in a total concentration of 0 to 80%, and
  one or more compounds according to formulas (III-1a) to (III-1e), (III-2a) to (III-2b), (III-3a-1) to (III-3a-6), (III-3b-1), (III-3c-1) to (III-3c-3), (IV-1a), (IV-1b) and (IV-2a) in a total concentration of 0 to 45%, where the total concentration of the compounds of the formulas (I) and (II) is between 40 and 100%.

In a further preferred embodiment of the invention, the liquid-crystalline medium comprises (liquid-crystalline medium II)
- one or more compounds according to formulas (I-1a) to (I-1c), (I-2a) to (I-2c), (I-3a) to (I-3c) and (I-4a) to (I-4c) in a total concentration of 5 to 60%
- one or more compounds according to formulas (II-2a), (II-3b), (II-3e) and (II-3h) in a total concentration of 0 to 80%,
- one or more compounds according to formulas (II-1a) and (II-1b) in a total concentration of 1 to 80%, and
- one or more compounds according to formulas (III-1a) to (III-1e), (III-2a) to (III-2b), (III-3a) to (III-3c), (IV-1a), (IV-1b) and (IV-2a) in a total concentration of 0 to 45%, where the total concentration of the compounds of the formulas (I) and (II) is between 40 and 100%.

In a more preferred embodiment of the invention, the liquid-crystalline medium comprises (preferred liquid-crystalline medium II)
- one or more compounds according to formulas (I-1a) to (I-1c) in a total concentration of 5 to 60%
- one or more compounds according to formulas (II-2a-1), (II-3b-1) to (II-3b-3), (II-3e-1) and (II-3h-1) in a total concentration of 0 to 80%,
- one or more compounds according to formulas (II-1a-1) to (II-1a-3) and (II-1b-1) in a total concentration of 1 to 80%, and
- one or more compounds according to formulas (III-1a) to (III-1e), (III-2a) to (III-2b), (III-3a-1) to (III-3a-6), (III-3b-1), (III-3c-1) to (III-3c-3), (IV-1a), (IV-1b) and (IV-2a) in a total concentration of 0 to 45%, where the total concentration of the compounds of the formulas (I) and (II) is between 40 and 100%.

In a further preferred embodiment of the invention, the liquid-crystalline medium comprises (liquid-crystalline medium III)
- one or more compounds according to formulas (I-1a) to (I-1c), (I-2a) to (I-2c), (I-3a) to (I-3c) and (I-4a) to (I-4c) in a total concentration of 5 to 60%
- one or more compounds according to formulas (II-1e), (II-2a), (II-3a), (II-3b), (II-3e) and (II-3h) in a total concentration of 5 to 80%,
- one or more compounds according to formulas (III-1a) to (III-1e), (III-2a) to (III-2b), (III-3a) to (III-3c), (IV-1a), (IV-1b) and (IV-2a) in a total concentration of 0 to 45%, where the total concentration of the compounds of the formulas (I) and (II) is between 40 and 100%.

In a more preferred embodiment of the invention, the liquid-crystalline medium comprises (preferred liquid-crystalline medium III)
- one or more compounds according to formulas (I-1a) to (I-1c) in a total concentration of 5 to 60%
- one or more compounds according to formulas (II-1e-1), (II-2a-1), (II-3a-1) to (II-3a-2), (II-3b-1) to (II-3b-3), (II-3e-1) and (II-3h-1) in a total concentration of 5 to 80%,
- one or more compounds according to formulas (III-1a) to (III-1e), (III-2a) to (III-2b), (III-3a-1) to (III-3a-6), (III-3b-1), (III-3c-1) to (III-3c-3), (IV-1a), (IV-1b) and (IV-2a) in a total concentration of 0 to 45%, where the total concentration of the compounds of the formulas (I) and (II) is between 40 and 100%.

In a further preferred embodiment of the invention, the liquid-crystalline medium comprises (liquid-crystalline medium IV)
- one or more compounds according to formulas (I-1a) to (I-1c), (I-2a) to (I-2c), (I-3a) to (I-3c) and (I-4a) to (I-4c) in a total concentration of 5 to 60%
- one or more compounds according to formulas (II-2a), (II-3b), (II-3e) and (II-3h) in a total concentration of 5 to 80%,
- one or more compounds according to formulas (II-1a) to (III-1e), (III-2a) to (III-2b), (III-3a) to (III-3c), (I V-1a), (IV-1b) and (IV-2a) in a total concentration of 0 to 45%, where the total concentration of the compounds of the formulas (I) and (II) is between 40 and 100%.

In a more preferred embodiment of the invention, the liquid-crystalline medium comprises (preferred liquid-crystalline medium IV)
- one or more compounds according to formulas (I-1a) to (I-1c) in a total concentration of 5 to 60%
- one or more compounds according to formulas (II-2a-1), (II-3b-1) to (II-3b-3), (II-3e-1) and (II-3h-1) in a total concentration of 5 to 80%,
- one or more compounds according to formulas (III-1a) to (III-1e), (III-2a) to (III-2b), (III-3a-1) to (III-3a-6), (III-3b-1), (III-3c-1) to (III-3c-3), (IV-1a), (IV-1b) and (IV-2a) in a total concentration of 0 to 45%, where the total concentration of the compounds of the formulas (I) and (II) is between 40 and 100%.

The liquid crystal media according to the present invention consist of several compounds, preferably of 5 to 30, more preferably of 6 to 20 and most preferably of 6 to 16 compounds. These compounds are mixed according to methods known in the art. As a rule, the required amount of the compound used in the smaller amount is dissolved in the compound used in the greater amount. In case the temperature is above the clearing point of the compound used in the higher concentration, it is particularly easy to observe completion of the process of dissolution. It is, however, also possible to prepare the media by other conventional ways, e.g. using so called pre-mixtures, which can be e.g. homologous or eutectic mixtures of compounds or using so called multi-bottle-systems, the constituents of which are ready to use mixtures themselves.

The invention concerns furthermore a process for the preparation of a liquid-crystalline medium as defined above, characterized in that one or more compounds of the formula (I) are mixed with one or more compounds of the formula (II) and optionally with one or more further mesogenic compounds and/or additives.

According to a preferred embodiment of the invention, the switch element comprises
- the liquid-crystalline medium in the form of a thin layer, and
- at least two polarisers, preferably in the form of thin layers, one of them positioned on one side of the liquid-crystalline medium, the other positioned on the opposite side of the liquid-crystalline medium.

The polarisers can be linear or circular polarisers, preferably linear polarisers.

For linear polarisers, it is preferred that the directions of polarisation of the two polarisers are rotated with respect to each other by a defined angle.

Further layers and/or elements, such as one or more separate alignment layers, one or more glass sheets, one or more bandblock filters and/or color filters to block light of certain wavelengths, for example UV-light, may be present. Furthermore, one or more insulating layers, such as low-emissivity films, for example, may be present. Additionally, one or more adhesive layers, one ore more protective layers, one or more passivation layers and one or more barrier layers may be present. Optionally, a metal oxide layer, where the metal oxide may comprise two or more different metals and where the metal oxide may be doped with halogenide ions, preferably fluoride, may be present. Preferred is a metal oxide layer comprising one or more of the following: indium tin oxide (ITO), antimony tin oxide (ATO), aluminium zinc oxide (AZO), $SnO_2$ and $SnO_2$:F (fluorine doped $SnO_2$). Particularly preferred is a metal oxide layer comprising ITO.

In the layer of the liquid crystalline medium, spacers may be present. Typical embodiments of the above-mentioned elements as well as their function is known to the person skilled in the art.

For the purposes of this application, the term "polariser" refers to a device or substance which blocks light of one polarisation direction and transmits light of another polarisation direction. Likewise, the term "polariser" refers to a device or substance which blocks light of one kind of circular polarisation (right-handed or left-handed) whereas it transmits light of the other kind of circular polarisation (left-handed or right-handed).

The blocking may occur by reflection and/or absorption. A reflective polariser therefore reflects light of one polarisation direction or one kind of circular polarisation and transmits light of the opposite polarisation direction or other kind of circular polarisation; and an absorptive polariser absorbs light of one polarisation direction or one kind of circular polarisation and transmits light of the opposite polarisation direction or other kind of circular polarisation. The reflection or absorption is typically not quantitative, leading to the polarisation of light by the polariser not being perfect.

According to the present invention, both absorptive and reflective polarisers may be used in the switch element. Preferably, the polarisers according to the invention represent optical thin films. Examples of reflective polarisers which can be used according to the invention are DRPF (diffusive reflective polariser film, by 3M), DBEF (dual brightness enhanced film, by 3M), layered-polymer distributed Bragg reflectors (DBR) as described in U.S. Pat. No. 7,038,745 and U.S. Pat. No. 6,099,758 and APF (advanced polariser film, by 3M). Furthermore, wire-grid-polarisers (WGP), which reflect infrared light, as described in U.S. Pat. No. 4,512,638, for example, may be used. Wire-grid polarizers which reflect in the visible and ultraviolet part of the spectrum are described in U.S. Pat. No. 6,122,103, for example, and may also be used according to the invention. Examples of absorptive polarisers which may be used according to the invention are Itos XP38 polarising film or Nitto Denko GU-1220DUN polarising film. Examples of circular polarisers which can be used according to the invention are APNCP37-035-STD (left handed) and APNCP37-035-RH (right handed) from American Polarizers Inc.

According to the invention, the switch element is thermoresponsive, signifying that its switching state is determined by temperature. In a preferred embodiment of the invention, no electrical wiring, circuitry and/or switching network is present in the switch element.

The switching of the switch element occurs between a bright or open state of the switch element in which a higher proportion of radiant energy is transmitted and a dark or shut state of the switch element in which a smaller proportion of radiant energy is transmitted.

Radiant energy is defined as above and is understood to comprise electromagnetic radiation in the UV-A region, VIS region and near-infrared region. Naturally, the switch element is not equally effective over the complete spectrum of radiant energy as defined above. Preferably, the switch element blocks a high proportion of NIR and VIS-light in the shut state, particularly preferably a high proportion of NIR light.

Also preferred are switch elements that switch in one of the ranges VIS or NIR only as well as combinations switching in one range and permanently blocking the other, for example switching VIS and permanently blocking NIR.

According to a preferred embodiment of the invention, the switching is effected by a change in the physical condition of the liquid-crystalline medium. This change in the physical condition of the liquid-crystalline medium is temperature-dependent. Preferably, it is a phase transition. According to a particularly preferred embodiment of the invention, the switching is effected by a phase transition of the liquid-crystalline medium from a liquid-crystalline phase to an isotropic phase which takes place at a particular temperature. Even more preferably, the switching is effected by a phase transition of the liquid-crystalline medium from a nematic phase to an isotropic phase.

Typically, the liquid-crystalline medium is in the isotropic state at a temperature above the phase-transition temperature and in a liquid-crystalline, preferably nematic state at a temperature below the phase-transition temperature.

Since the switching of the device is due to a temperature-dependent change in the physical condition of the liquid-crystalline medium, the liquid-crystalline medium represents the thermoresponsive element of the optical switch. However, further thermoresponsive elements may be present.

For the use of the switch to regulate the radiation energy flow between an interior space and the environment, preferably between a room of a building and the exterior, it is desirable that the switch operates at a temperature which is typical for the exterior of buildings. Preferably, the switching temperature of the switch element is between −20 and 80° C., more preferably between 10 and 60° C. and most preferably between 20 and 40° C.

The switching temperature is defined to be the temperature of the switch element. Typically, this temperature is similar to the outside air temperature. However, under some conditions, for example under direct exposure to sunlight, it may differ significantly from the outside air temperature. Also, in the case of certain device setups, for example when the switch element is located inside of an insulated glass unit, the temperature of the switch element may differ significantly from the outside air temperature.

According to a preferred embodiment of the invention, as stated above, the switching of the switch element is effected by a change in the physical condition of the liquid-crystalline medium. More preferably, this change in physical condition represents a phase transition which takes place at a certain phase transition temperature. Preferably, the phase transition temperature is between −20 and 80° C., more preferably between 10 and 60° C. and most preferably between 20 and 40° C.

In a highly preferred embodiment of the present invention, the plane of polarisation of polarised light is rotated by the liquid-crystalline medium by a defined value if it is in the liquid-crystalline state. In contrast, the plane of polarisation of polarised light is not rotated by the liquid-crystalline medium if it is in the isotropic state. It is a further aspect of this preferred embodiment, that the directions of polarisation of the polarisers are not identical to each other, but rotated against each other by a defined angle.

In this preferred embodiment, the two states of the device are characterized as follows:

In the bright or open state, incoming light is polarised linearly by the first polariser. The linearly polarised light then passes through the liquid-crystalline medium in its liquid-crystalline state, which leads to its direction of polarisation being rotated by a defined angle.

After passing the liquid-crystalline medium, the linearly polarised light then hits the second polariser. A defined fraction of the light hitting the polariser is transmitted through the polariser. Preferably, there is an identity or only a relatively small divergence, most preferably an identity of the value by which the planes of polarisation of the two polarisers are rotated against each other and the value by which the plane of polarisation of the polarised light is rotated by the liquid-crystalline medium in its nematic state.

Here, the value by which the plane of polarisation of the polarised light is rotated by the liquid-crystalline medium is understood to be the angle formed between the plane of polarisation before entering the medium and the plane of polarisation after leaving the medium. This angle can in principle be between 0° and 180°. According to this, a turn by an angle X being larger than 180° is equivalent to a turn by X minus n*180°, the integer n being chosen so that the resulting angle X' is in the range 0°≤X'>180°.

However, it is to be noted that the liquid-crystalline medium may cause a twisting of the plane of polarisation of the polarised light passing it which has an absolute value larger than 180°. Even a rotation by more than one complete turn) (360°, for example 2¼ turns or 3¾ turns may occur according to the invention. However, the net value by which the plane of polarisation of polarised light is rotated from entering to leaving the liquid-crystalline medium is still in any case between 0° and 180°, as has been explained above.

Obviously, depending on the reference system used, the angle by which the plane of polarisation is rotated may also be represented as ranging from −90° to 90°, negative values meaning right-turns, positive values meaning left-turns.

In the bright state, due to the small divergence between the value by which the planes of polarisation of the two polarisers are rotated against each other and the value by which the plane of polarisation of the polarised light is rotated by the liquid-crystalline medium, a large fraction of the light which has passed the first polariser also passes the second polariser.

In order for the above-described bright state to occur, it is required that the liquid-crystalline medium is in its liquid-crystalline state. Typically, this is the case at a temperature below the phase-transition temperature. Therefore, according to this preferred embodiment, the switch element is in the bright state, when it is at a temperature which is below the switching temperature.

In order for the dark transparent or shut state to occur, it is required that the liquid-crystalline medium is in the isotropic state. In this case, incoming light is again linearly polarised by the first polariser. The polarised light then passes through the liquid-crystalline medium being in its isotropic state. The liquid-crystalline medium in the isotropic state does not rotate the direction of polarisation of linearly polarised light.

After passing the liquid-crystalline medium, the linearly polarised light with its direction of polarisation maintained hits the second polariser. The direction of polarisation of the second polariser is, as described above, rotated with respect to the direction of polarisation of the first polariser, which is in this case, as explained above, also the direction of polarisation of the linearly polarised light hitting the second polariser.

Due to the directions of polarisation of the polarized light and the polariser not being coincident, but rotated with respect to each other by a defined value which identical to the value by which the two polarisers are rotated against each other, only a fraction of the light is now transmitted. The amount of light transmitted in this state is smaller than the amount of light transmitted in the bright state.

As described above, in the dark or shut state, the liquid-crystalline medium is in its isotropic state. Typically, this is the case at a temperature above the phase-transition temperature. Therefore, according to this preferred embodiment, the switch element is in the dark or shut state, when it is at a temperature which is above the switching temperature.

The directions of polarisation of the two polarisers may be rotated with respect to each other by any arbitrary value, depending on the desired transmission of the switch element in the dark transparent state. Preferred values are in the range of 45° to 135°, more preferred 70° to 110°, most preferred 80° to 100°.

The value by which the liquid-crystalline medium in its nematic state rotates the plane of polarisation of polarised light does not have to be identical to the value by which the directions of polarisation of the two polarisers are rotated with respect to each other. Preferably, the values are similar, with a preferred deviation of very preferably less than 30° and most preferably less than 20°.

The value by which the liquid-crystalline medium in its nematic state rotates the plane of polarisation of polarised light is preferably in the range of 0° to 360°. However, values of larger than 360° may also be present according to the invention.

For the purpose of regulating the temperature of the interior of buildings, the setup described above is generally preferred. At low temperatures, the flow of radiant energy is allowed since the switch element is in the open state. This leads to an increase in the heat uptake of the building, reducing heating costs. At high temperatures, the switch element is in the shut state, limiting the flow of radiant energy into the building. This decreases unwanted heat uptake at high temperatures, reducing the costs for air conditioning.

Depending on the angle by which the two polarisers are offset against each other, and also depending on whether the polarisers polarise all of the incoming light or only a fraction of it, more or less light is transmitted through the switch element in the shut state. With perfect polarisers in a "crossed" position (direction of polarisation rotated by 90° against each other), no light is transmitted in the shut state. If the direction of polarisation of the polarisers is rotated by an angle different than 90°, some light is transmitted even in the shut state. Such an arrangement is desirable according to the invention.

Similarly, the amount of light which is transmitted through the switch element in the open state depends, among other factors, on the efficiency of the polarisers and on the difference between the angle by which the liquid-crystalline medium rotates the direction of polarisation of linearly polarised light and the angle by which the directions of polarisation of the two polarisers are rotated against each other. With perfect polarisers and an exact congruence of the angles of rotation, up to 50% of the light is transmitted through the device in the open state and, ideally, 0% of the light is transmitted in the shut state.

The rejection of 50% of the light is due to the fact that a perfect linear polariser rejects (by absorption or reflection) 50% of incoming unpolarised light. The transmittance of light through the device can therefore be raised significantly if non-perfect polarisers are used, which may be desirable.

It should be mentioned here that numerous other combinations of polariser orientations and rotation of the direction of polarised light due to the liquid-crystal medium can be used within the present invention.

Other embodiments of the present invention comprise a liquid-crystalline medium which scatters light when it is within a first temperature range and which is transparent within a second temperature range, whereas this second temperature range may be above or below the first temperature range. According to another embodiment of the present invention, the liquid-crystalline medium may affect the polarisation state of circularly polarised light.

According to a further embodiment of the present invention, the liquid-crystalline medium represents a guest-host system which comprises, in addition to one or more liquid-crystalline compounds, dye molecules or other materials which show absorptive or reflective properties. According to this embodiment, the liquid-crystalline medium provides orientation for the dye molecules when in the liquid-crystalline state (low temperature), but does not provide such orientation when in the isotropic state (high temperature). Since the dye molecules interact with light in a different manner depending on their degree of orientation, the guest-host-system shows temperature-dependent transmission properties. According to the present invention, when the liquid-crystalline medium represents a guest-host system, it may be preferable to use only one polarizer or no polarizer at all in the devices according to the invention. Furthermore according to the present invention, when the liquid-crystalline medium represents a guest-host system, a twisted nematic orientation of the liquid-crystalline medium or a vertically aligned orientation of the liquid-crystalline medium is preferably used.

According to a preferred embodiment of the invention, the rotation of polarised light by the liquid-crystalline medium in the liquid-crystalline state is caused by an alignment of the molecules of the liquid-crystalline medium. According to the invention, this alignment is typically effected by alignment layers which are in direct contact with the liquid-crystalline medium. Preferentially, the alignment layers represent the two outer boundaries of the liquid-crystalline medium layer. For example, two alignment layers facing each other may be attached to the interior of the compartment enclosing the liquid-crystalline medium. According to another preferred embodiment, the alignment layers constitute the compartment enclosing the liquid-crystalline medium. The alignment layers may be prepared by rubbing a polymer or polymer film with a rubbing cloth, a sandpaper or some other suitable material. Polyimide films are particularly suitable for this, but orientation may be achieved also on other kinds of polymers.

According to a further preferred embodiment, the alignment layer and the polariser layer are not separate but form one single layer. They may, for example, be glued or laminated together. The property of inducing an alignment of the liquid-crystalline molecules may for example be conferred to the polariser by rubbing, scratching and/or micropatterning the polariser layer. For details, it is referred to patent application US 2010/0045924, whose disclosure is hereby incorporated by reference.

A preferred embodiment of the switch element according to the invention comprises the liquid-crystalline medium within a container of transparent material, preferably a transparent polymer or glass.

Furthermore, the switch element comprises two or more alignment layers which are in direct contact with the liquid-crystalline medium. For example, the aligment layers can be attached to the inner surface of the above-mentioned container. According to another preferred embodiment, the inner container surface can serve as an alignment layer itself.

Furthermore, the switch element comprises two or more polarisers which may be present in the form of polarising foils, as disclosed above. Further rigid or flexible layers may be present, such as additional glass sheets, bandblock filters such as UV-blocking films and/or insulating layers such as low-emissivity films. According to this embodiment of the invention, the switch element is rigid and cannot be bent or rolled up for storage and/or transport due to the presence of layers of rigid material.

According to another preferred embodiment of the invention, the liquid-crystalline medium is enclosed by a flexible polymer sheet. This flexible polymer sheet may represent the polariser and/or the alignment layer. Further layers, such as described above, may be additionally present. For details, it is referred to patent application US 2010/0045924, whose disclosure is hereby incorporated by reference. According to this embodiment, the switch element is flexible and can be bent and/or rolled up.

According to another preferred embodiment of the invention, the liquid-crystalline medium has a solid or gel-like consistency. According to this embodiment, a rigid container for the liquid-crystalline medium is not required, eliminating the need for glass and/or rigid polymer sheets to be present in the switch element. An advantage of this embodiment of the invention is that the switch element is less vulnerable to damage and can be produced in the form of thin flexible sheets which can be rolled up. The switch element can then be cut from this roll in any shape or size, which simplifies storage, transport and production of the device.

To obtain the above-mentioned solid or gel-like consistency of the liquid-crystalline medium, the following procedures can be used according to the invention.

The liquid-crystalline medium may, for example, be embedded in the form of discrete compartments such as microdroplets of liquid-crystalline medium, within an optically transparent medium. The optically transparent medium preferably is a polymeric material, particularly preferably an isotropic thermoplastic, duroplastic or elastomeric polymer. Particularly preferably, the polymeric material is a thermoplastic or elastomeric polymer.

Examples for this are NCAP-films (NCAP=nematic curvilinear aligned phases) and PDLC-films (PDLC=polymer dispersed liquid crystal). NCAP films may be obtained by a process in which the encapsulating polymeric material, for example polyvinyl alcohol, the liquid-crystalline medium and a carrier material, such as water, are mixed thoroughly in a colloid mill.

Afterwards, the carrier material is removed, for example by evaporation. A detailed procedure for the formation of NCAP-films is described in U.S. Pat. No. 4,435,047.

PDLC-films, which are described for example in U.S. Pat. No. 4,688,900; WO 89/06264; EP 0272585 and Mol. Cryst. Liq. Cryst. Nonlin. Optic, 157, (1988), 427-441, may be obtained by homogeneously mixing the liquid-crystalline medium with monomers and/or oligomers which will later react to the polymer matrix. After polymerisation, a phase separation is induced, in which compartments or microdroplets of liquid crystalline medium form, which are dispersed within the polymer matrix.

According to another embodiment of the invention, the liquid-crystalline medium is present as a continuous phase within a polymer network (PN-systems). Such systems are described in detail in EP 452460, EP 313053 and EP 359146, for example. The polymer network typically has a spongy structure, in which the liquid-crystalline medium can float freely. According to a preferred embodiment, it is formed by polymerisation of mono- or polyacrylate monomers.

Preferably, the liquid-crystalline medium is present in PN-systems in a percentage of more than 60%, particularly preferably in a percentage of 70-95%. The polymer network systems can be prepared by inducing a polymerisation reaction in a mixture comprising the liquid-crystalline medium and the respective monomers and/or oligomers which form the three-dimensional polymer network. According to a preferred embodiment, the polymerisation is started by photo-initiation.

According to another embodiment of the invention, the polymer does not form a network, but is dispersed in the form of small particles within the liquid-crystalline medium, which is present as a continuous phase as in PN-network systems.

The liquid-crystalline media according to the present invention are particularly suitable for use in the above-mentioned PDLC-, NCAP- and PN-systems.

Further subject of the present invention is therefore a composite system comprising a liquid-crystalline medium as defined above and a polymer, preferably a microporous polymer.

According to the present invention, the switch element can be attached to transparent windows, facades, doors or roofs of any kind, including those present in private, public and commercial builings, in containers for transport, storage and inhabitation and in any vehicles. Particularly preferred is the attachment to insulated glass units (IGU) or multipane windows and/or the use as an integrated element of insulated glass units or multipane windows. According to a preferred embodiment of the invention, the switch element is attached at the outside-facing side of the window, facade, door or roof. According to another preferred embodiment, the switch element is placed in the interior of an IGU, where it is protected from adverse effects such as extreme weather conditions and from degradation due to UV exposure. In an alternative embodiment, the switch element is attached at the inside-facing side of the window, facade, door or roof.

According to one embodiment of the invention, the switch element covers the complete surface of the window. In this case, the control over the radiant energy flow by the switching of the device is maximised.

According to another embodiment of the invention, the switch element covers only parts of the surface of the window, so that there are gaps left which are not covered by the switch element. These gaps may take the form of stripes, spots and/or larger areas. This could allow that some parts of a window can be switched between a bright state and a dark state, whereas other parts remain bright at all times. This leads to the transparency of the window especially in the shut state to be increased.

The switch element may be used according to the invention to regulate the radiant energy flow between an interior space and the environment. Particularly preferably, it is used for regulating the energy flow in the form of VIS-light and NIR-light or VIS-light only or combinations of regulated VIS-light and permanently blocked NIR-light. It is furthermore preferred that the switch element regulates the radiant energy flow automatically, without the need for manual controlling, by its capability of temperature-dependent switching between an open state and a shut state. According to a particularly preferred embodiment of the invention, the switch element is used to regulate the interior temperature of a building and/or a vehicle.

For the purposes of the present invention, all concentrations are, unless explicitly noted otherwise, indicated in mass percent and relate to the corresponding mixture or mixture component, unless explicitly indicated otherwise.

The clearing points of liquid-crystalline mixtures are determined in capillary tubes. A suitable instrument is Mettler Toledo FP90. Typically, liquid-crystalline mixtures show a clearing range. According to our definition, the clearing point is the lowest temperature of that range where the whole material is still nematic.

Alternatively, clearing points of a mixture in a display can be determined in normally white-mode TN-cells in a microscope hot stage. The beginning of the transition from the nematic to the isotropic state leads to black spots in the TN-cell. When heating up, the temperature at which such spots first occur is determined to be the clearing point.

For applications according to the present invention, long-term storage behaviour of the liquid-crystalline media in displays is relevant. For determination of the long-term storage behaviour in displays, the liquid-crystalline mixture is filled into several TN-cells with a thickness of 5 to 6 μm. The TN-cells receive an end-seal, get polarisers attached for normally white mode setup and are stored for up to 1000 hours in a refrigerator at a given temperature. At defined time intervals, the TN-cells are inspected visually for dark spots indicating crystallisation or smectic-nematic transitions. If the TN-cells do not show spots at the end of the testing period, the test is passed. Otherwise, the time elapsed until the first spots are detected is noted as a measure of long-term storage stability.

In the present application and especially in the following examples, the structures of the liquid crystal compounds are represented by abbreviations, which are also called "acronyms". Tables A to C show the structural elements of the compounds together with their corresponding abbreviations.

All groups $C_nH_{2n+1}$, $C_mH_{2m+1}$, $C_pH_{2p+1}$ and $C_qH_{2q+1}$ are preferably straight chain alkyl groups with n, m, p and q C-atoms, respectively. All groups $C_nH_{2n}$, $C_mH_{2m}$, $C_pH_{2p}$ and $C_kH_{2q}$ are preferably $(CH_2)_n$, $(CH_2)_m$, $(CH_2)_p$ and $(CH_2)_q$, respectively; and —CH=CH— preferably is trans-respectively E vinylene. The Indices n, m, p and q preferably have a value between 1 and 10.

Remark: From left side to right side in the chemical structure, the indices used are n, if only one index occurs; n and m if two indices occur; n, m and p if three indices occur; and n, m, p and q if four indices occur. This nomenclature may be extended if necessary.

Therefore, a right-hand-side alkyl group —$C_nH_{2n+1}$ corresponding to -n according to the acronym nomenclature (see table below) may also be a group —$C_mH_{2m+1}$ corresponding to -m, or a group —$C_pH_{2p+1}$ corresponding to -p, or a group —$C_qH_{2q+1}$ corresponding to -q, depending on the index which is chosen. The same applies for all other groups of Table C where a letter n is used signifying an alkyl group having n carbon atoms and 2n+1 hydrogen atoms or an alkylene group having n carbon atoms and 2n hydrogen atoms.

Table A lists the symbols used for the ring elements, table B those for the linking groups and table C those for the symbols for the left hand and the right hand end groups of the molecules.

TABLE A

Ring Elements

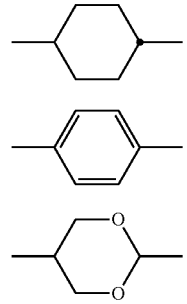

C

P

D

TABLE A-continued

Ring Elements

| Label | Structure |
|---|---|
| Dl | 1,3-dioxane ring |
| A | tetrahydropyran (O at position 1) |
| AI | tetrahydropyran (inverted) |
| G | 3-fluoro-1,4-phenylene |
| GI | 2-fluoro-1,4-phenylene (inverted) |
| U | 2,3-difluoro-1,4-phenylene |
| UI | 2,5-difluoro-1,4-phenylene |
| Y | 2,3-difluoro-1,4-phenylene (alt.) |
| M | pyrimidine-2,5-diyl |
| MI | pyrimidine-2,5-diyl (inverted) |
| N | pyridine-2,5-diyl |
| NI | pyridine-2,5-diyl (inverted) |
| Np | naphthalene-2,6-diyl |
| n3f | trifluoronaphthalene-2,6-diyl |
| n3fI | trifluoronaphthalene-2,6-diyl (inverted) |
| Th | tetrahydronaphthalene-2,6-diyl |
| thI | tetrahydronaphthalene-2,6-diyl (inverted) |
| th2f | difluoro-tetrahydronaphthalene-2,6-diyl |
| th2fI | difluoro-tetrahydronaphthalene-2,6-diyl (inverted) |
| o2f | difluoro-chromane-2,6-diyl |
| o2fI | difluoro-chromane-2,6-diyl (inverted) |
| Dh | decahydronaphthalene-2,6-diyl |

TABLE A-continued

Ring Elements

| | |
|---|---|
| K | (structure) |
| KI | (structure) |
| L | (structure) |
| LI | (structure) |
| F | (structure) |
| FI | (structure) |

TABLE B

Linking Groups

| | |
|---|---|
| E | $-CH_2-CH_2-$ |
| V | $-CH=CH-$ |
| T | $-C\equiv C-$ |
| W | $-CF_2-CF_2-$ |
| B | $-CF=CF-$ |
| Z | $-CO-O-$ |
| X | $-CF=CH-$ |
| O | $-CH_2-O-$ |
| Q | $-CF_2-O-$ |
| ZI | $-O-CO-$ |
| XI | $-CH=CF-$ |
| OI | $-O-CH_2-$ |
| QI | $-O-CF_2-$ |

TABLE C

End Groups

| Left hand side, used alone or in combination with others | | Right hand side, used alone or in combination with others | |
|---|---|---|---|
| -n- | $C_nH_{2n+1}-$ | -n | $-C_nH_{2n+1}$ |
| —nO— | $C_nH_{2n+1}-O-$ | —On | $-O-C_nH_{2n+1}$ |
| —V— | $CH_2=CH-$ | —V | $-CH=CH_2$ |
| —nV— | $C_nH_{2n+1}-CH=CH-$ | —nV | $-C_nH_{2n}-CH=CH_2$ |
| —Vn— | $CH_2=CH-C_nH_{2n}-$ | —Vn | $-CH=CH-C_nH_{2n+1}$ |
| —nVm— | $C_nH_{2n+1}-CH=CH-C_mH_{2m}-$ | —nVm | $-C_nH_{2n}-CH=CH-C_mH_{2m+1}$ |
| —N— | $N\equiv C-$ | —N | $-C\equiv N$ |
| —S— | $S=C=N-$ | —S | $-N=C=S$ |
| —F— | $F-$ | —F | $-F$ |
| —CL— | $Cl-$ | —CL | $-Cl$ |
| -M- | $CFH_2-$ | -M | $-CFH_2$ |
| -D- | $CF_2H-$ | -D | $-CF_2H$ |
| -T- | $CF_3-$ | -T | $-CF_3$ |
| —MO— | $CFH_2O-$ | —OM | $-OCFH_2$ |
| —DO— | $CF_2HO-$ | —OD | $-OCF_2H$ |
| —TO— | $CF_3O-$ | —OT | $-OCF_3$ |
| -A- | $H-C\equiv C-$ | -A | $-C\equiv C-H$ |
| -nA- | $C_nH_{2n+1}-C\equiv C-$ | -An | $-C\equiv C-C_nH_{2n+1}$ |
| —NA— | $N\equiv C-C\equiv C-$ | —AN | $-C\equiv C-C\equiv N$ |

| Left hand side, used in combination with others only | | Right hand side, used in combination with others only | |
|---|---|---|---|
| -...n...- | $-C_nH_{2n}-$ | -...n... | $-C_nH_{2n}-$ |
| -...M...- | $-CFH-$ | -...M... | $-CFH-$ |
| -...D...- | $-CF_2-$ | -...D... | $-CF_2-$ |
| -...V...- | $-CH=CH-$ | -...V... | $-CH=CH-$ |
| -...Z...- | $-CO-O-$ | -...Z... | $-CO-O-$ |
| -...ZI...- | $-O-CO-$ | -...ZI... | $-O-CO-$ |
| -...K...- | $-CO-$ | -...K... | $-CO-$ |
| -...W...- | $-CF=CF-$ | -...W... | $-CF=CF-$ | wherein n and m each are integers and three points "..." indicate that other symbols of this table may be present at the position.

TABLE D1
Illustrative Structures
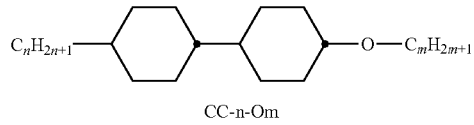
CC-n-Om
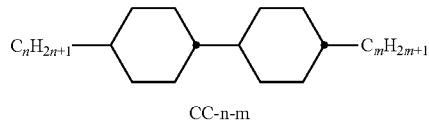
CC-n-m
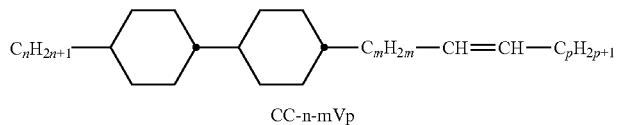
CC-n-mVp
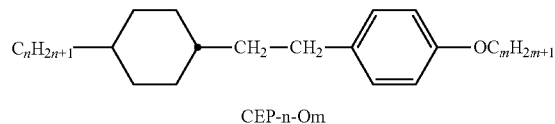
CEP-n-Om
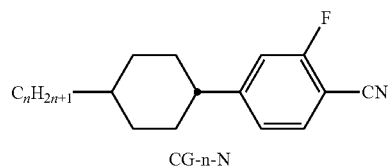
CG-n-N
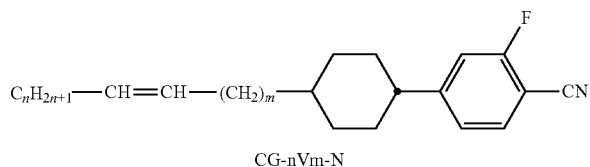
CG-nVm-N
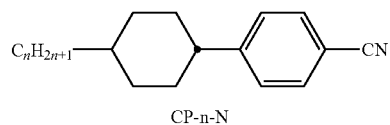
CP-n-N
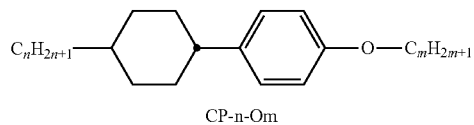
CP-n-Om
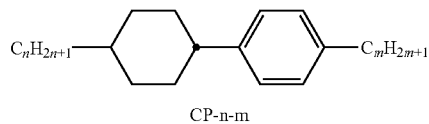
CP-n-m
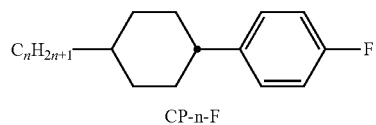
CP-n-F

TABLE D1-continued

Illustrative Structures $C_nH_{2n+1}$—CH=CH—$(CH_2)_m$—⟨cyclohexyl⟩—⟨phenyl⟩—CN CP-nVm-N $C_nH_{2n+1}$—⟨cyclohexyl⟩—⟨phenyl(2,6-F)⟩—CN CU-n-N $C_nH_{2n+1}$—⟨cyclohexyl⟩—CO—O—⟨cyclohexyl⟩—$C_mH_{2m+1}$ CZC-n-m $C_nH_{2n+1}$—O—$C_mH_{2m}$—⟨cyclohexyl⟩—CO—O—⟨cyclohexyl⟩—$C_pH_{2p+1}$ CZC-nOm-p $C_nH_{2n+1}$—⟨cyclohexyl⟩—CO—O—⟨cyclohexyl⟩—O—$C_mH_{2m+1}$ CZC-n-Om $C_nH_{2n+1}$—O—⟨cyclohexyl⟩—CO—O—⟨cyclohexyl⟩—$C_mH_{2m+1}$ CZC-nO-m $C_nH_{2n+1}$—O—⟨cyclohexyl⟩—CO—O—⟨cyclohexyl⟩—O—$C_mH_{2m+1}$ CZC-nO—Om $C_nH_{2n+1}$—CH=CH—$(CH_2)_m$—⟨cyclohexyl⟩—CO—O—⟨cyclohexyl⟩—$C_pH_{2p+1}$ CZC-nVm-p $CH_2$=CH—$C_mH_{2m}$—⟨cyclohexyl⟩—CO—O—⟨cyclohexyl⟩—$C_pH_{2p+1}$ CZC—Vm-p $C_nH_{2n+1}$—⟨cyclohexyl⟩—CO—O—⟨cyclohexyl⟩—$C_mH_{2m}$—CH=$CH_2$ CZC-n-mV $C_nH_{2n+1}$—CH=CH—$C_mH_{2m}$—⟨cyclohexyl⟩—CO—O—⟨cyclohexyl⟩—$C_pH_{2p}$—CH=CH—$C_qH_{2q+1}$ CZC-nVm-pVq TABLE D1-continued
Illustrative Structures
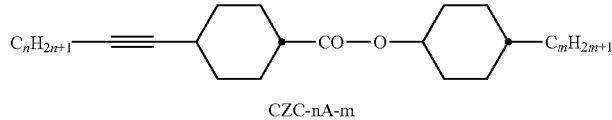
CZC-nA-m
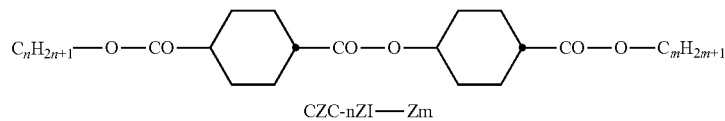
CZC-nZI—Zm
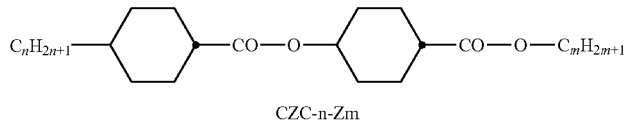
CZC-n-Zm
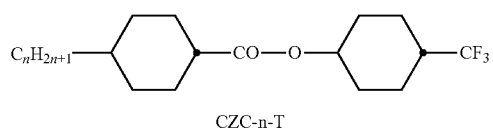
CZC-n-T
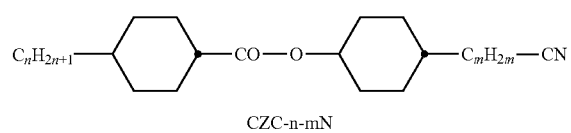
CZC-n-mN
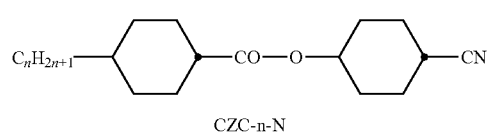
CZC-n-N
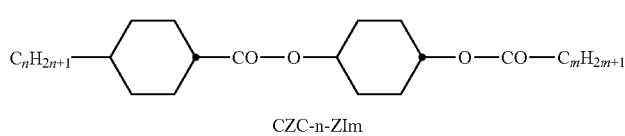
CZC-n-ZIm
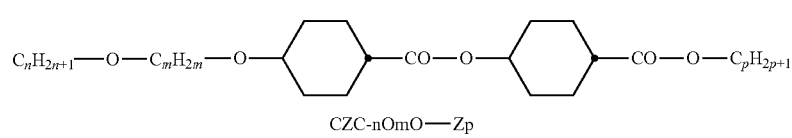
CZC-nOmO—Zp
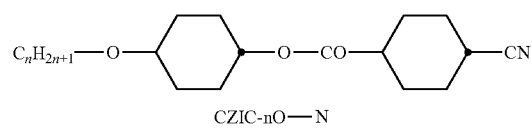
CZIC-nO—N
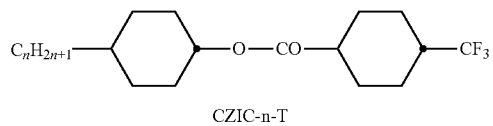
CZIC-n-T
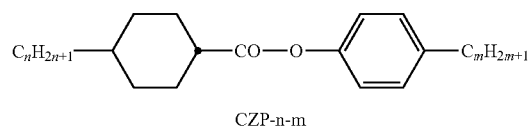
CZP-n-m TABLE D1-continued
Illustrative Structures
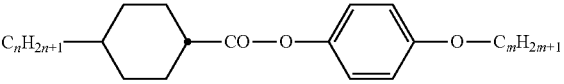
CZP-n-Om
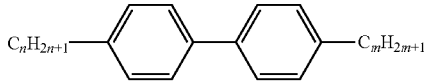
PP-n-m
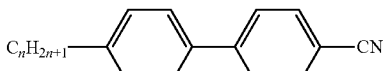
PP-n-N
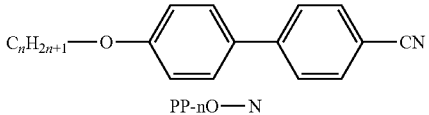
PP-nO—N
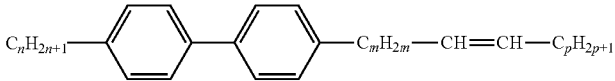
PP-n-mVp
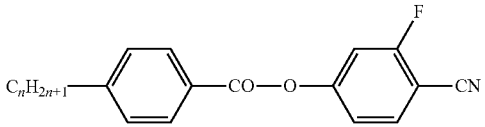
PZG-n-N
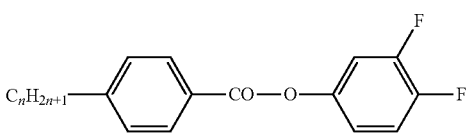
PZG-n-F
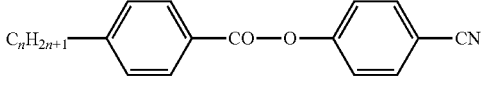
PZP-n-N
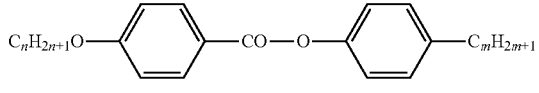
PZP-nO-m
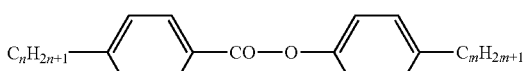
PZP-n-m TABLE D1-continued
Illustrative Structures
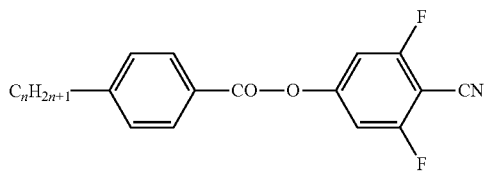
PZU-n-N
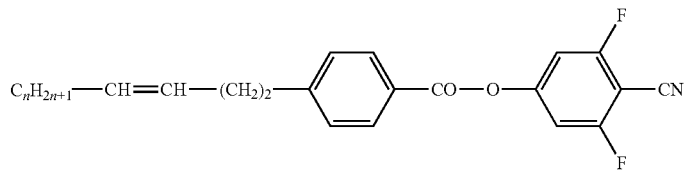
PZU-nV2—N
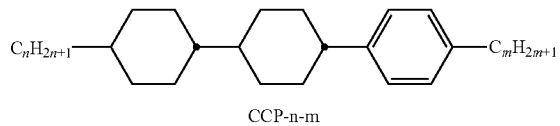
CCP-n-m
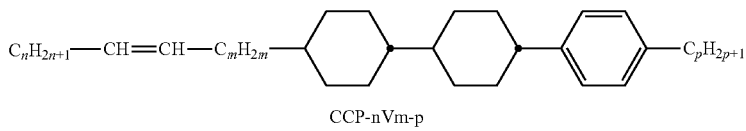
CCP-nVm-p
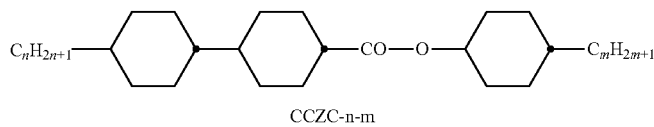
CCZC-n-m
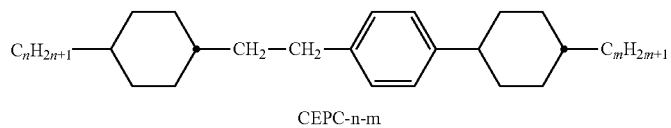
CEPC-n-m
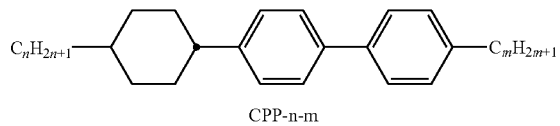
CPP-n-m
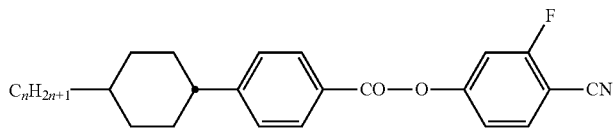
CPZG-n-N
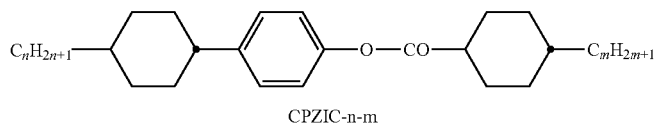
CPZIC-n-m
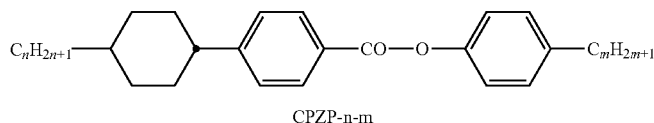
CPZP-n-m TABLE D1-continued
Illustrative Structures
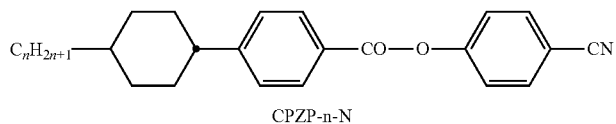
CPZP-n-N
CZCEC-n-m
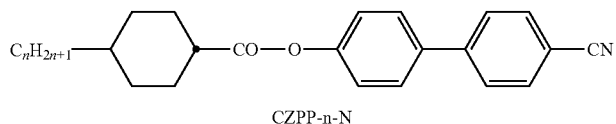
CZPP-n-N
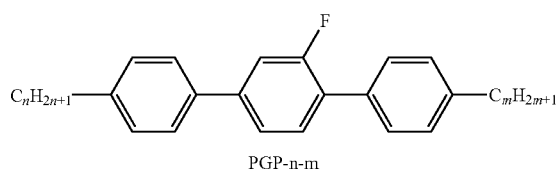
PGP-n-m
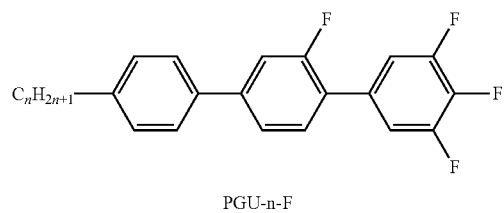
PGU-n-F
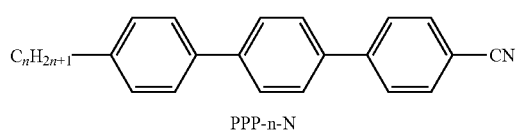
PPP-n-N
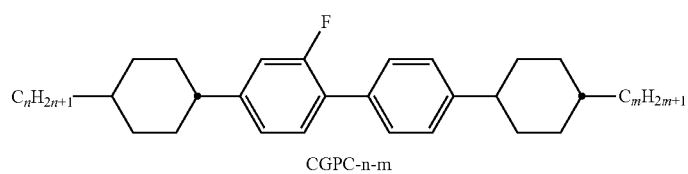
CGPC-n-m
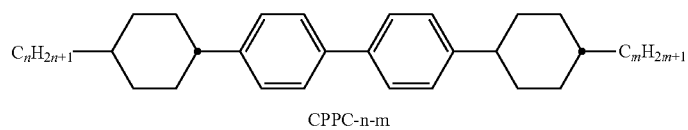
CPPC-n-m TABLE D2
Further Illustrative Structures
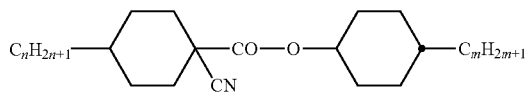
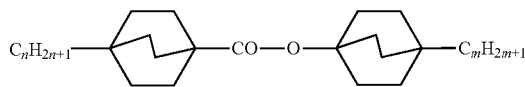
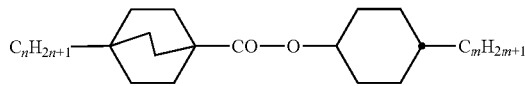
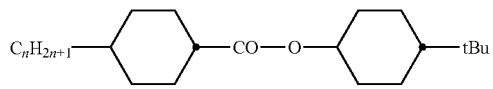
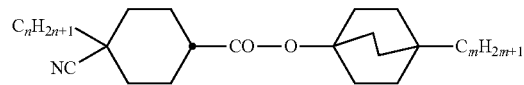
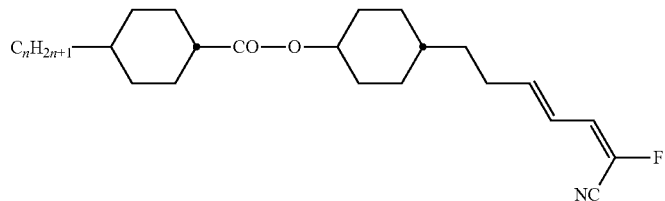
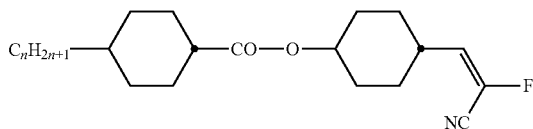
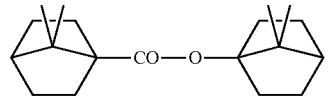 [SMILES: CC1(C)C2CCC1(OC(=O)C13CCC(CC1)C3(C)C)CC2]
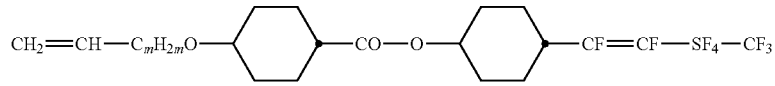
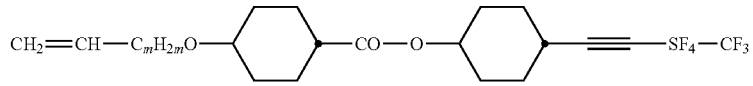

Table E lists chiral dopants, which are preferably used in the liquid crystalline media according to the present invention.
TABLE E
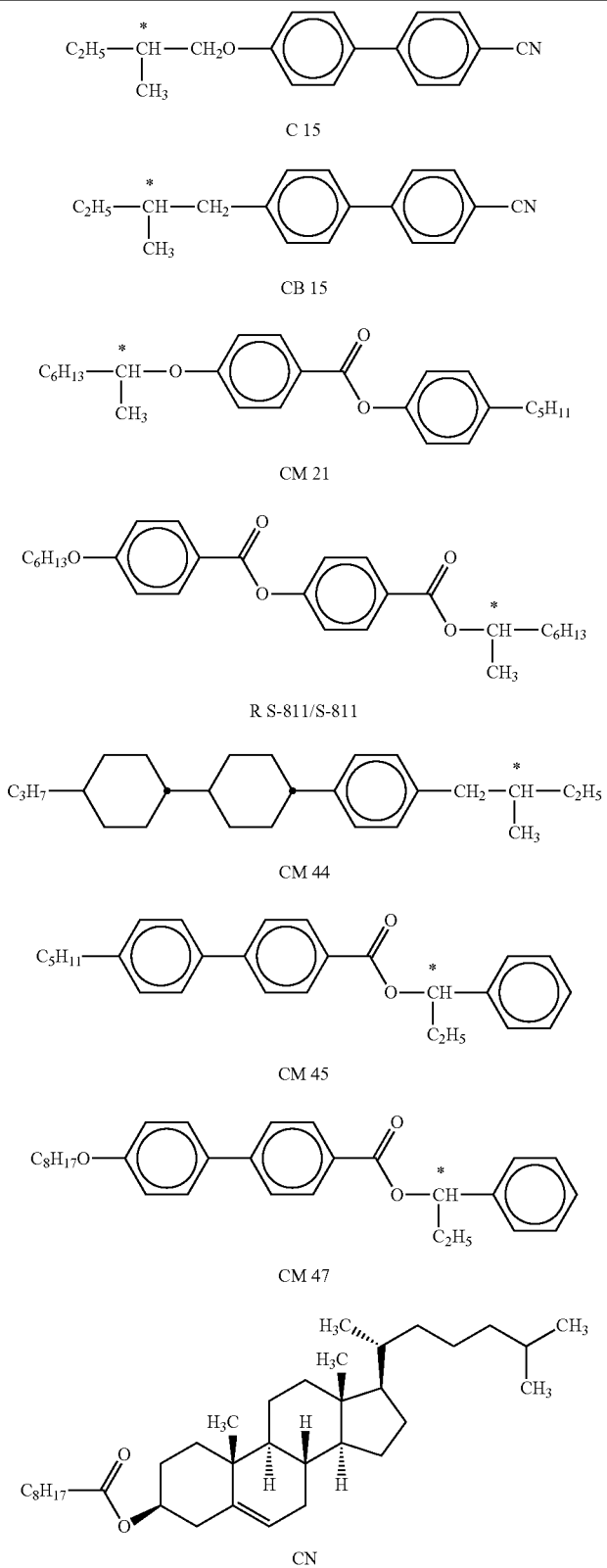

TABLE E-continued
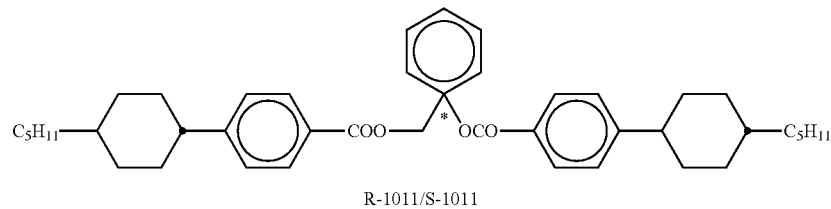
R-1011/S-1011
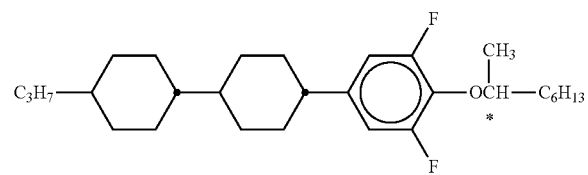
R-2011/S-2011
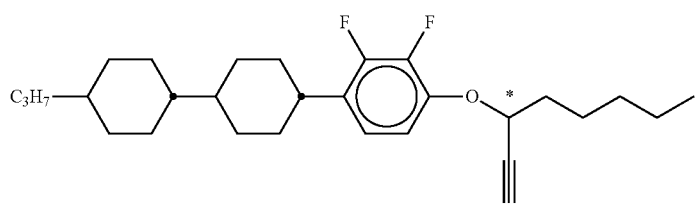
R-3011/S-3011
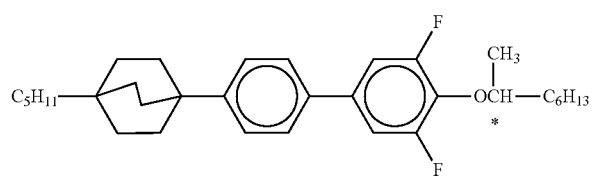
R-4011/S-4011
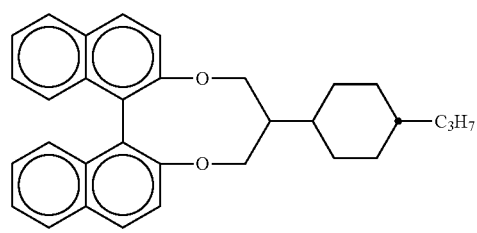
R-5011/S-5011

In a preferred embodiment of the present invention the media according to the present invention comprise one or more compounds selected from the group of compounds of table E.

Table F lists stabilizers, which are preferably used in the liquid crystalline media according to the present invention.

TABLE F

Remark: In this table "n" means an integer in the range from 1 to 12.

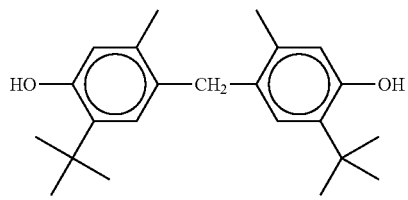

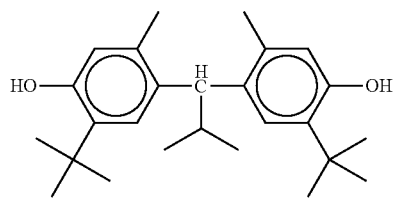

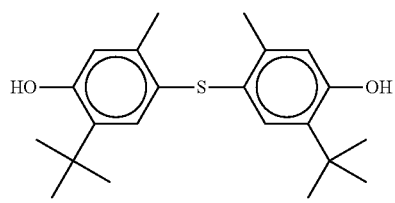

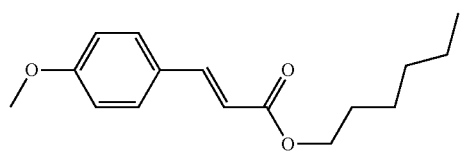 [SMILES: CCCCCCOC(=O)/C=C/c1ccc(OC)cc1]

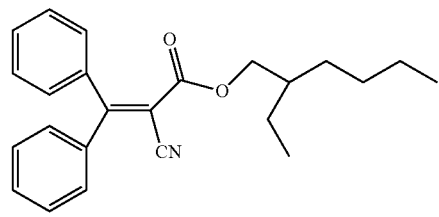 [SMILES: CCCCC(CC)COC(=O)C(C#N)=C(c1ccccc1)c1ccccc1]

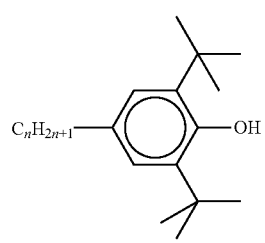

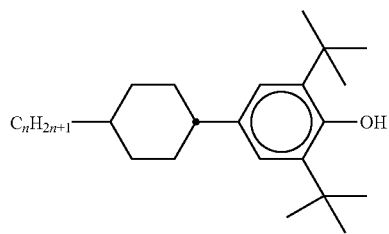

TABLE F-continued
Remark: In this table "n" means an integer in the range from 1 to 12.
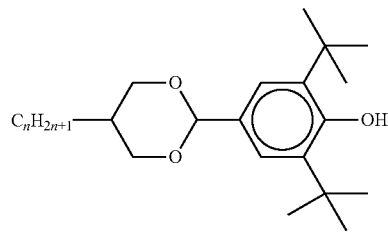
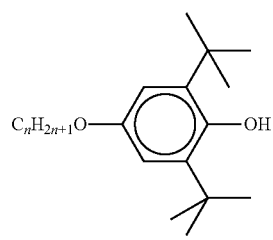
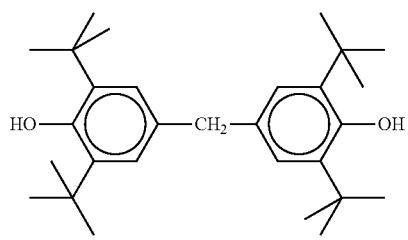
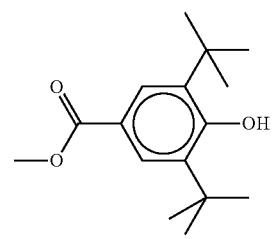
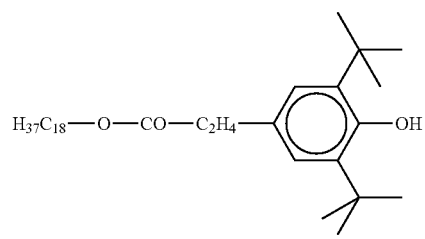
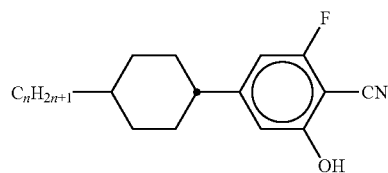

TABLE F-continued
Remark: In this table "n" means an integer in the range from 1 to 12.
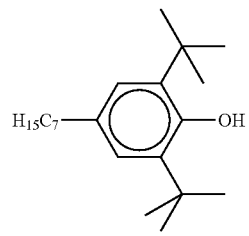
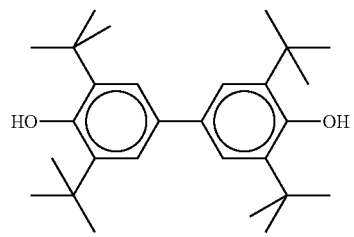
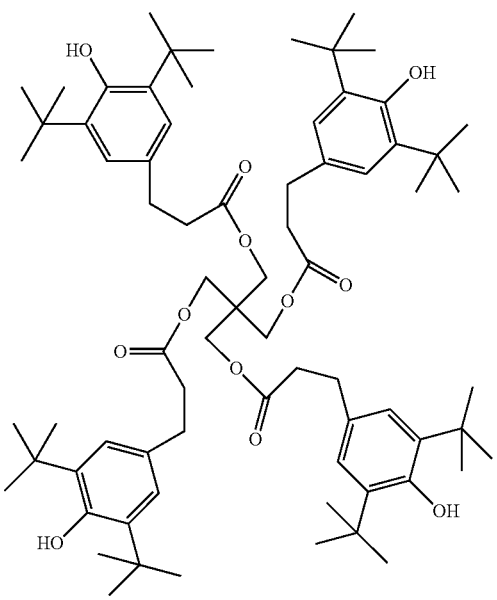 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
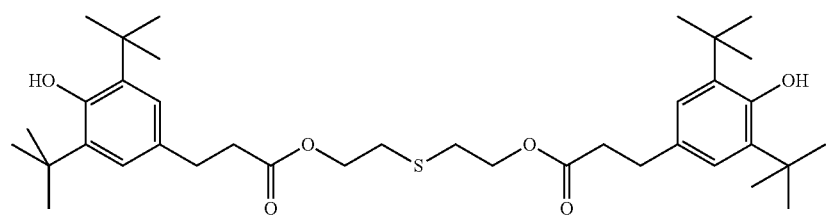 [SMILES: CC(C)(C)c1cc(CCC(=O)OCCSCCOC(=O)CCc2cc(C(C)(C)C)c(O)c(C(C)(C)C)c2)cc(C(C)(C)C)c1O]

TABLE F-continued
Remark: In this table "n" means an integer in the range from 1 to 12.
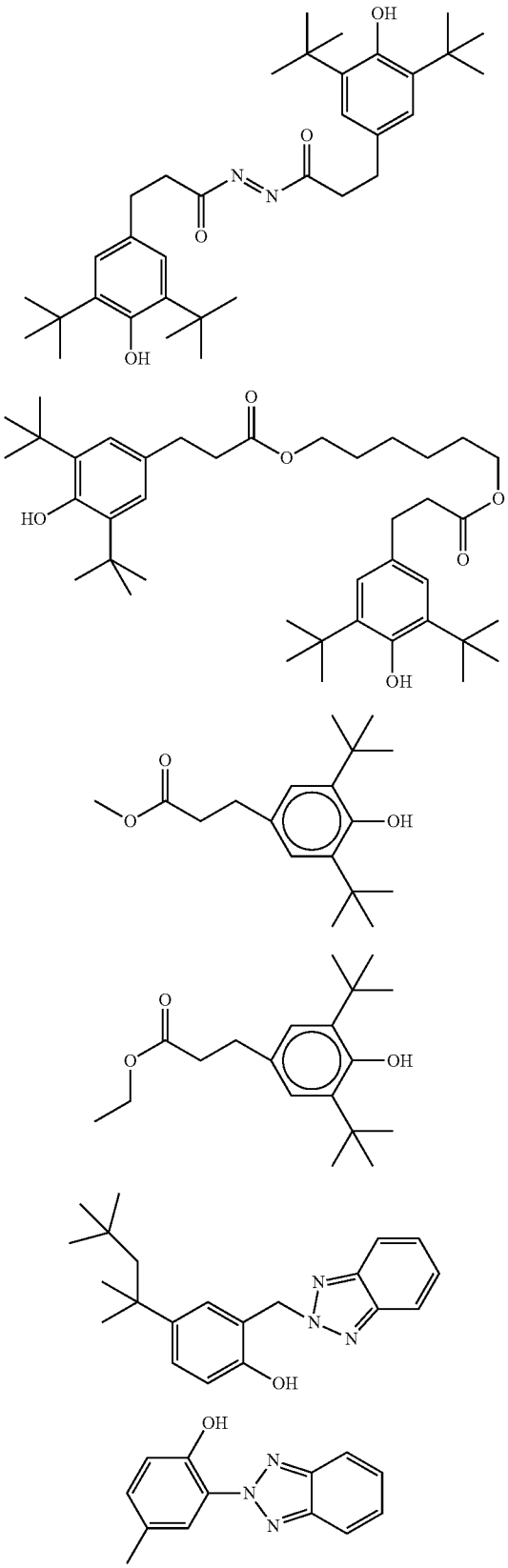

TABLE F-continued
Remark: In this table "n" means an integer in the range from 1 to 12.
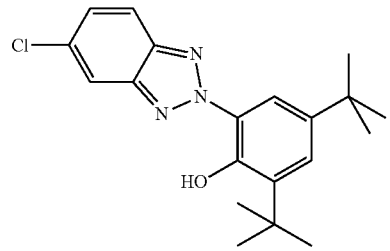 [SMILES: CC(C)(C)c1cc(-n2nc3ccc(Cl)cc3n2)c(O)c(C(C)(C)C)c1]
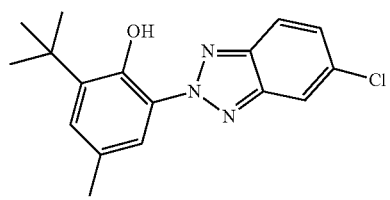 [SMILES: Cc1cc(-n2nc3ccc(Cl)cc3n2)c(O)c(C(C)(C)C)c1]
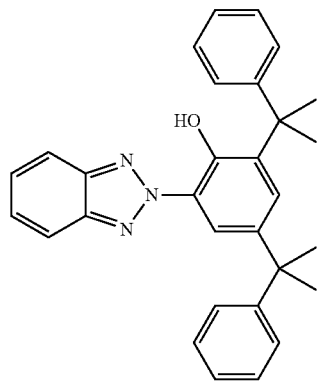 [SMILES: CC(C)(c1ccccc1)c1cc(-n2nc3ccccc3n2)c(O)c(C(C)(C)c2ccccc2)c1]
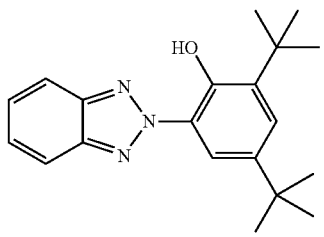 [SMILES: CC(C)(C)c1cc(-n2nc3ccccc3n2)c(O)c(C(C)(C)C)c1]
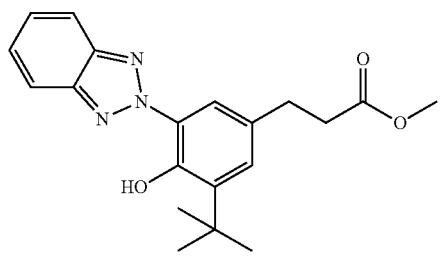 [SMILES: COC(=O)CCc1cc(-n2nc3ccccc3n2)c(O)c(C(C)(C)C)c1]

TABLE F-continued
Remark: In this table "n" means an integer in the range from 1 to 12.
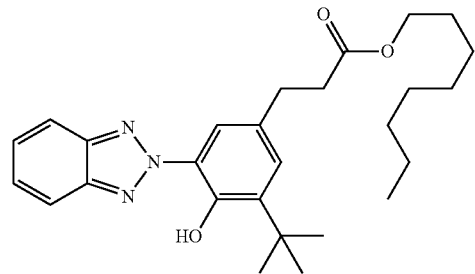 [SMILES: CCCCCCCCOC(=O)CCc1cc(-n2nc3ccccc3n2)c(O)c(C(C)(C)C)c1]
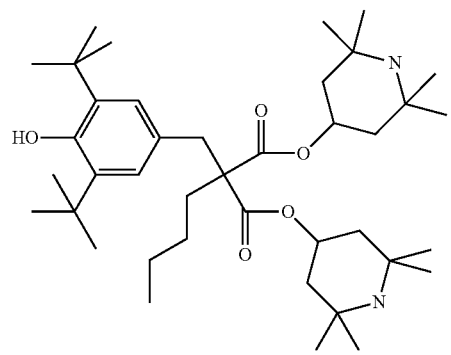 [SMILES: CCCCC(Cc1cc(C(C)(C)C)c(O)c(C(C)(C)C)c1)(C(=O)OC1CC(C)(C)NC(C)(C)C1)C(=O)OC1CC(C)(C)NC(C)(C)C1]
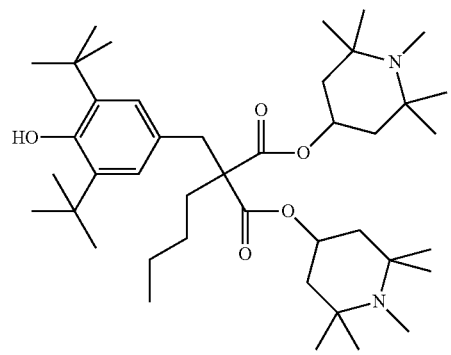 [SMILES: CCCCC(Cc1cc(C(C)(C)C)c(O)c(C(C)(C)C)c1)(C(=O)OC1CC(C)(C)N(C)C(C)(C)C1)C(=O)OC1CC(C)(C)N(C)C(C)(C)C1]
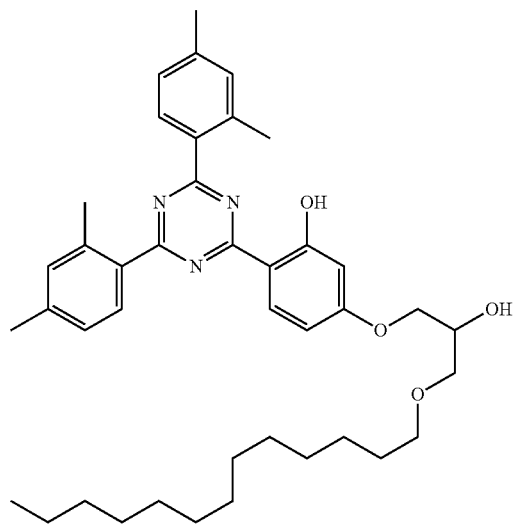 [SMILES: CCCCCCCCCCCCCOCC(O)COc1ccc(-c2nc(-c3ccc(C)cc3C)nc(-c3ccc(C)cc3C)n2)c(O)c1]

TABLE F-continued
Remark: In this table "n" means an integer in the range from 1 to 12.
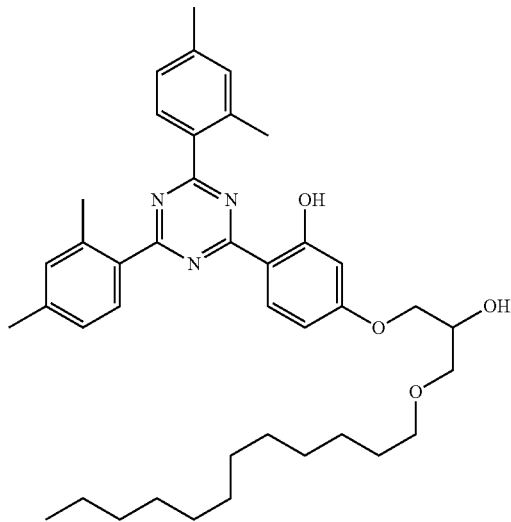 [SMILES: CCCCCCCCCCCCOCC(O)COc1ccc(-c2nc(-c3ccc(C)cc3C)nc(-c3ccc(C)cc3C)n2)c(O)c1]
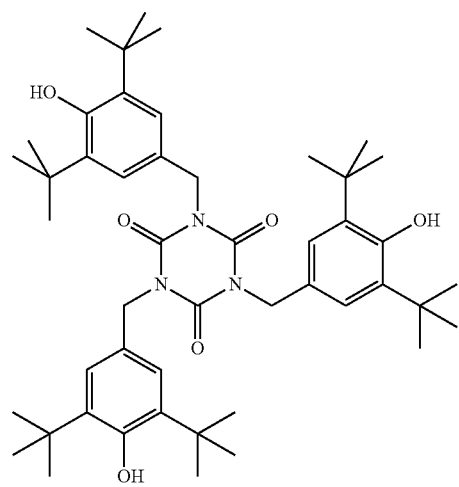 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
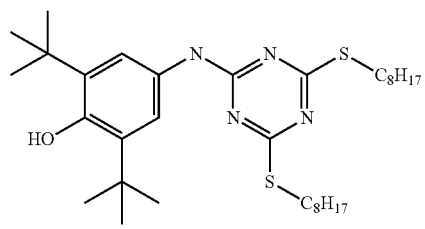

TABLE F-continued
Remark: In this table "n" means an integer in the range from 1 to 12.
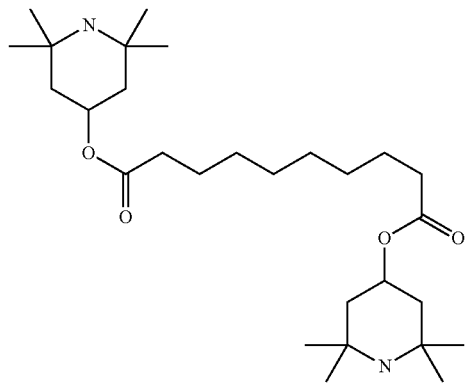
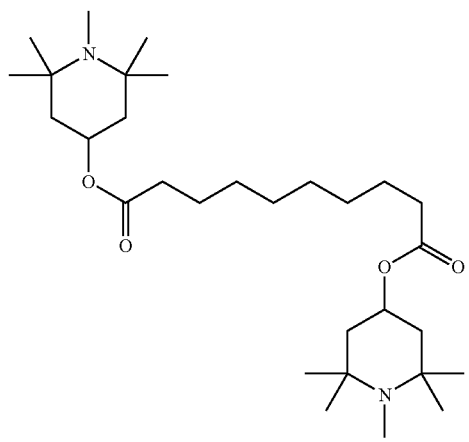
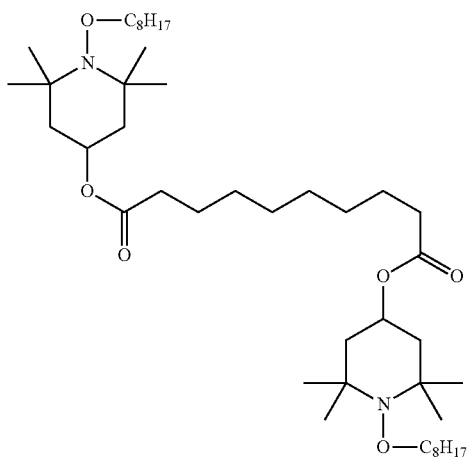
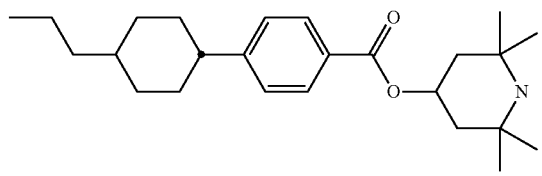

TABLE F-continued
Remark: In this table "n" means an integer in the range from 1 to 12.
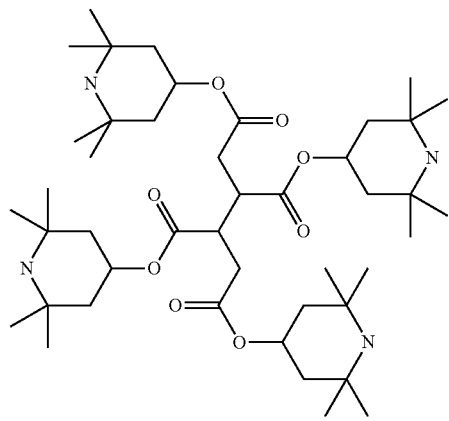
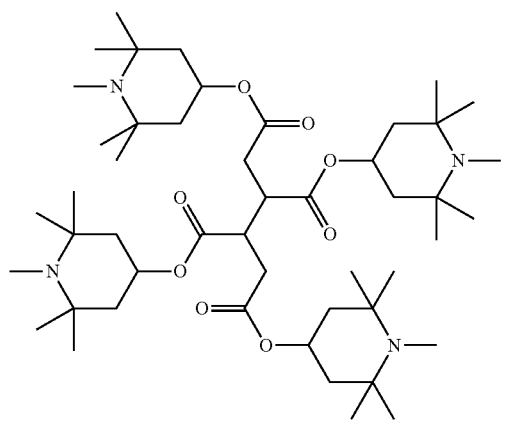
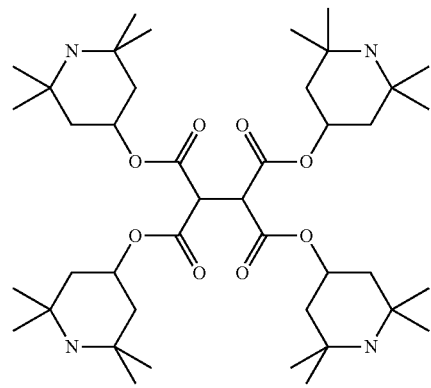

TABLE F-continued

Remark: In this table "n" means an integer in the range from 1 to 12.

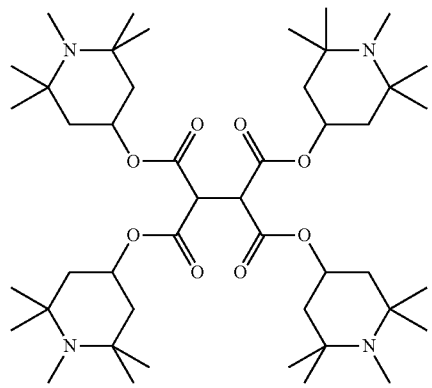

In a preferred embodiment of the present invention, the media according to the present invention comprise one or more compounds selected from the group of compounds of table F.

EXAMPLES

The following examplary liquid-crystalline mixtures are listed for the purpose of illustrating the present invention and are not to be understood as limiting it in any way.

The compositions of the liquid-crystalline mixtures are listed below together with their clearing points and their long-term-storage behaviour. The person skilled in the art learns from the data given below which properties can be obtained with the mixtures according to the invention. He is furthermore taught how the composition of the mixtures can be modified in order to obtain the desired properties, in particular a defined temperature of the clearing point and high long-term stability.

Liquid crystal mixtures with the compositions listed in the following tables are prepared, and their clearing points and long-term-storage behaviour are determined.

As stated in the description part of the present application, the clearing point of the liquid-crystalline media according to the invention is preferably between −20 and 80° C., more preferably between 10 and 60° C. and most preferably between 20 and 40° C.

Exemplary mixtures with a relatively high clearing point (>70° C., in particular >80° C.) are preferably used as a so-called two-bottle system in combination with a mixture having a lower clearing point.

1) Examples for Liquid-Crystalline Medium I

| Example-1 | | Example-2 | |
|---|---|---|---|
| Clearing point | | | |
| 72° C. | | 32° C. | |
| Storage stability at −40° C. | | | |
| >1000 h | | >1000 h | |
| Substance | % | Substance | % |
| CZC-5-3 | 6.2 | CZC-3-3 | 6 |
| PP-5-N | 10.6 | CZC-3-5 | 6 |
| CEP-5-O2 | 10.8 | CZC-5-3 | 6 |
| PZP-3-N | 4 | PP-5-N | 8 |
| PZP-4-N | 5 | CP-3-N | 9 |
| PZP-5-N | 5 | CP-3-O1 | 8 |
| CC-5-V | 7 | CP-5-3 | 13 |
| CZP-4-O2 | 11.5 | PZP-3-N | 3 |
| CZP-5-O1 | 11.5 | PZP-4-N | 3 |
| CZP-5-O3 | 11.3 | PZP-5-N | 3 |
| CZPP-2-N | 4.5 | CZP-3-O1 | 7 |
| CEPC-4-5 | 8.1 | CZP-4-O2 | 7 |
| PPP-5-N | 4.5 | CZP-5-O1 | 7 |
| | | CZP-5-O3 | 7 |
| | | CC-5-V | 7 |
| sum | 100 | | 100 |

2) Examples for Liquid-Crystalline Medium II

| Example-3 | | Example-4 | |
|---|---|---|---|
| Clearing point | | | |
| 72.5° C. | | 28° C. | |
| Storage stability at −40° C. | | | |
| >1000 h | | >1000 h | |
| Substance | % | Substance | % |
| CZC-3-5 | 8 | CZC-3-3 | 6 |
| CP-3-N | 10.5 | CZC-3-5 | 6 |
| CP-5-N | 5.5 | CZC-5-3 | 6 |
| CP-3-O1 | 5.5 | CP-3-N | 15 |
| PZP-2-N | 5 | CP-5-N | 14 |
| PZP-1O-1 | 15 | CP-3-O1 | 6 |
| PZP-1O-5 | 7 | CP-5-3 | 9 |
| PZP-6O-5 | 18 | PZP-1O-1 | 12 |
| CPZIC-3-4 | 4 | PZP-1O-5 | 12 |
| CPZIC-3-5 | 4 | PZP-6O-5 | 12 |
| CPZP-3-3 | 10 | CPZP-5-3 | 2 |
| CPZP-5-3 | 7.5 | | |
| sum | 100 | | 100 |

3) Examples for Liquid-Crystalline Medium III

|  | Example-5 |  | Example-6 |
|---|---|---|---|
|  | Clearing point |  |  |
|  | 66° C. |  | 34° C. |
|  | Storage stability at −40° C. |  |  |
|  | >1000 h |  | >1000 h |
| Substance | % | Substance | % |
| CZC-3-3 | 10 | CZC-3-3 | 6 |
| CP-3-N | 5 | CZC-3-5 | 6 |
| CP-3-O2 | 20 | CZC-3-5 | 6 |
| CP-3-O4 | 6 | CP-3-N | 16 |
| CC-3-O3 | 18 | CP-5-N | 6 |
| PZG-3-N | 2 | CP-3-O2 | 20 |
| PZG-3-N | 5 | CP-3-O4 | 6 |
| PZG-7-N | 5 | PZG-5-N | 5 |
| CCZC-3-3 | 3 | PZG-7-N | 5 |
| CCZC-3-5 | 4 | CC-3-O3 | 18 |
| CCZC-4-5 | 4 | CPP-5-2 | 6 |
| CPP-3-2 | 9 |  |  |
| CPP-5-2 | 9 |  |  |
| sum | 100 |  | 100 |

4) Examples for Liquid-Crystalline Medium IV

|  | Example-7 |  | Example-8 |
|---|---|---|---|
|  | Clearing point |  |  |
|  | 66° C. |  | 22° C. |
|  | Storage stability at −40° C. |  |  |
|  | >1000 h |  | >1000 h |
| Substance | % | Substance | % |
| CZC-3-3 | 14 | CZC-3-3 | 6 |
| CP-3-N | 15 | CZC-3-5 | 6 |
| CP-3-2 | 30 | CZC-5-3 | 6 |
| CPP-3-2 | 9 | CP-3-N | 15 |
| CPP-5-2 | 8 | CP-3-2 | 15 |
| CPZP-3-3 | 8 | CP-5-3 | 15 |
| CPZP-5-3 | 6 | CP-3-O1 | 14 |
| CPPC-3-3 | 4 | CPP-3-2 | 9 |
| CPPC-5-3 | 6 | CPP-5-2 | 8 |
|  |  | PZP-3-5 | 6 |
| SUM | 100 |  | 100 |

5) Use of Liquid-Crystalline Media in Switch Elements

The mixtures 1 to 8 according to the invention are employed as liquid-crystalline media in the switch element according to the procedure of US 2009/0015902.

For assembling the switch element, the procedure described in paragraphs [0050]-[0055] of the above-mentioned patent application is followed, except that instead of the mixture disclosed in the application (5 parts 6CB (4'-hexyl-4-cyanobiphenyl), 1.25 parts mixture E7 and 0.008 parts S-811) one of the exemplary mixtures of the present invention is used (examples 1-8).

With the mixtures according to the invention, switch elements with high operational lifetime can be obtained. The switch elements have a switching temperature which is close to the clearing point of the mixtures (10° C. to 80° C., which is in the preferred operating range of the elements). This shows that high device stability together with a controllable clearing point can be obtained with the mixtures according to the invention.

The invention claimed is:

1. A switch element, that is thermoresponsive and that switches between a less transmissive state for radiant energy and a more transmissive state for radiant energy, comprising in said element a liquid-crystalline medium, which comprises one or more compounds of formula (I)

formula (I)

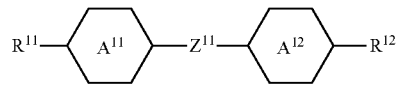

where $R^{11}$, $R^{12}$ are on each occurrence, identically or differently, are F, Cl, CN, NCS, $R^1$—O—CO—, $R^1$—CO—O—, an alkyl, alkoxy or thioalkoxy group having 1 to 10 C atoms or an alkenyl, alkenyloxy or thioalkenyloxy group having 2 to 10 C atoms, where one or more H atoms in the groups mentioned above may be replaced by F or Cl, and where one or more CH$_2$ groups in the groups mentioned above may be replaced by O, S, —O—CO— or —CO—O—; and where $R^1$ is, identically or differently on each occurrence, an alkyl or an alkenyl group having 1 to 10 C atoms, in which one or more H atoms may be replaced by F or Cl; and

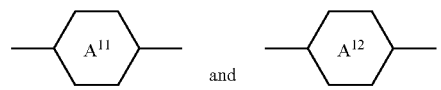

and

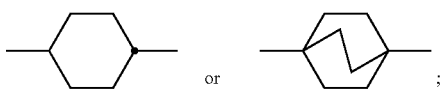

are and $Z^{11}$ is —CO—O— or —O—CO—, said liquid-crystalline medium having a clearing point lower than 50° C.

2. The switch element according to claim 1, wherein the liquid-crystalline medium additionally comprises one or more compounds of formula (II)

formula (II)

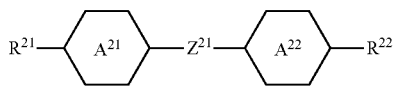

where $R^{21}$, $R^{22}$ have the meanings indicated for $R^{11}$ and $R^{12}$ in claim 1; and are

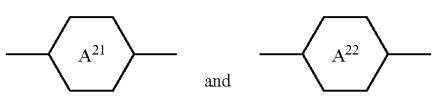

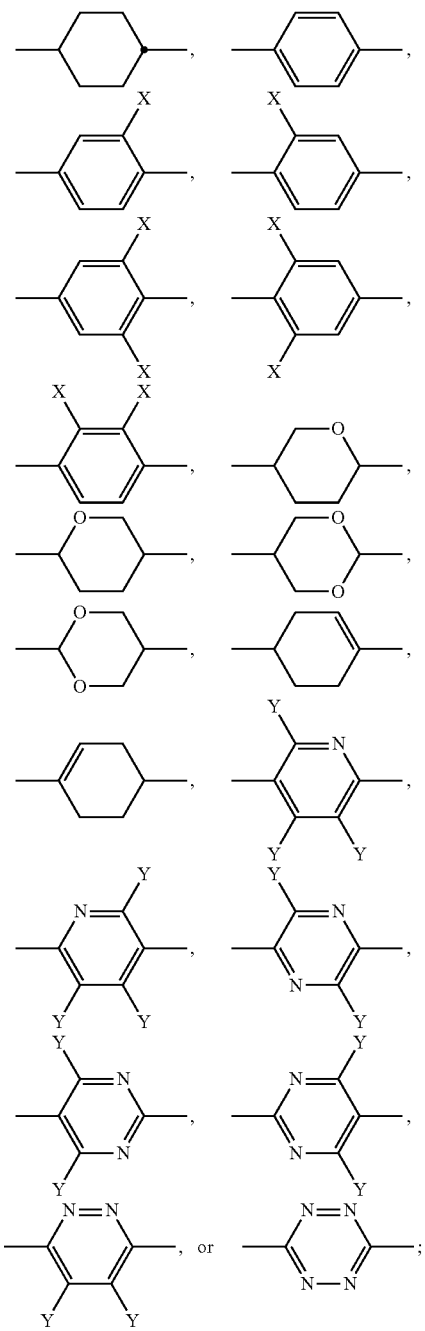

and

X is on each occurrence, identically or differently, F, Cl, CN or an alkyl, alkoxy or thioalkoxy group having 1 to 10 C atoms, where one or more H atoms in the groups mentioned above may be replaced by F or Cl and where one or more $CH_2$ groups may be replaced by O or S; and Y is on each occurrence, identically or differently, H or X; and $Z^{21}$ is —CO—O—, —O—CO—, —$CF_2$O—, —O$CF_2$—, —$CH_2CH_2$—, —O$CH_2$—, —$CH_2$O— or a single bond;

with the proviso that if

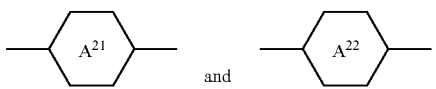

and are both selected to be

$Z^{21}$ is not —CO—O— or —O—CO—.

3. The switch element according to claim 1, wherein the liquid-crystalline medium additionally comprises one or more compounds of formulas (III) or (IV)

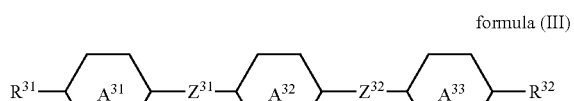

formula (III)

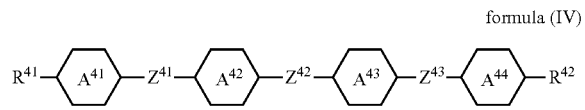

formula (IV)

where $R^{31}$, $R^{32}$, $R^{41}$ and $R^{42}$ have the meanings indicated for $R^{11}$ and $R^{12}$ in claim 1; and

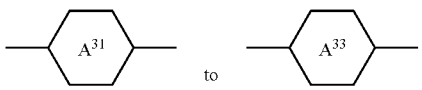

to are on each occurrence, identically or differently,

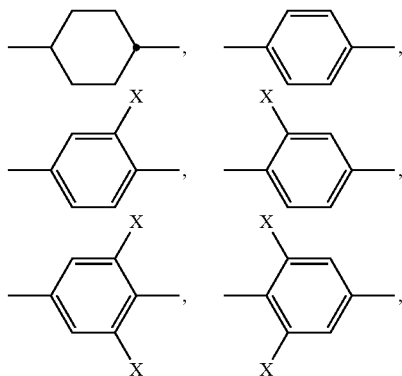

-continued

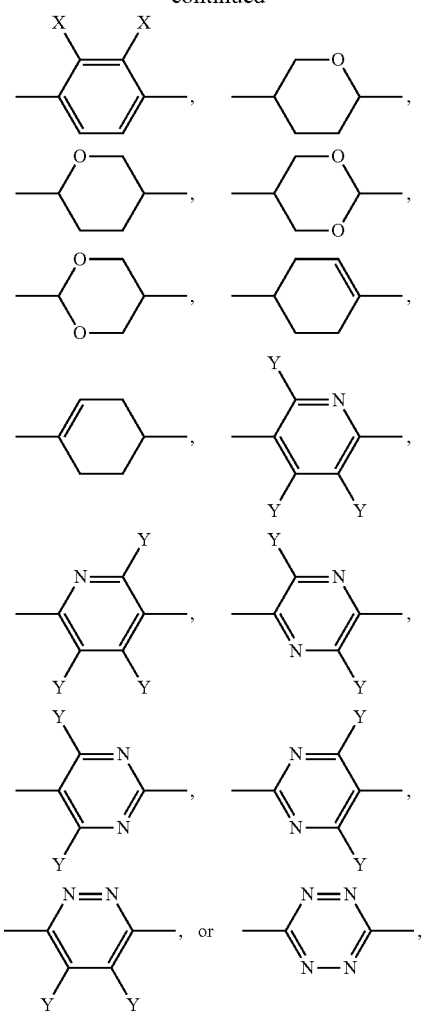

where X and Y are defined as in claim 1; and

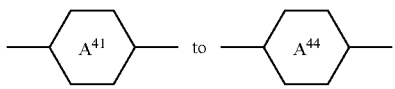

are on each occurrence, identically or differently,

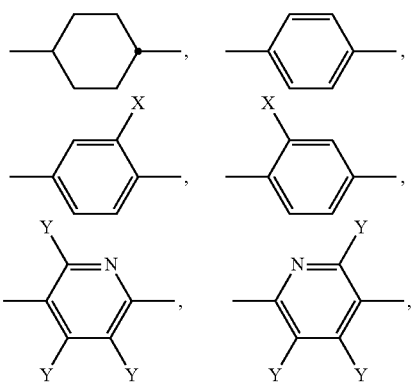

-continued

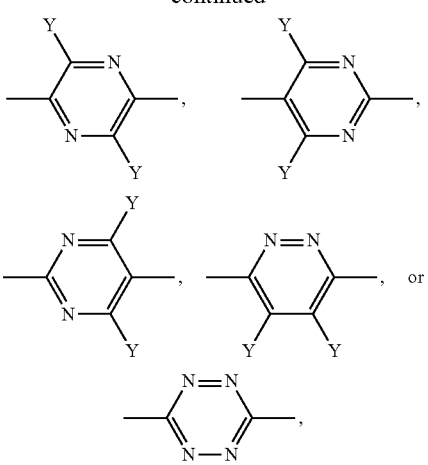

where X and Y are defined as in claim 1; and $Z^{31}$ and $Z^{32}$ are on each occurrence, identically or differently, —CO—O—, —O—CO—, —CF$_2$O—, —OCF$_2$—, —CH$_2$CH$_2$—, —OCH$_2$—, —CH$_2$O— or a single bond; and $Z^{41}$, $Z^{42}$ and $Z^{43}$ are on each occurrence, identically or differently, —CO—O—, —O—CO— or a single bond.

4. The switch element according to claim 1, wherein the compounds according to formula (I) are compounds according to at least one of formulas (I-1) to (I-4)

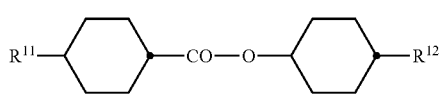
formula (I-1)

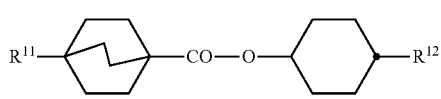
formula (I-2)

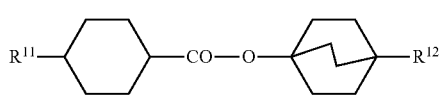
formula (I-3)

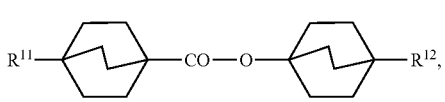
formula (I-4)

where $R^{11}$ and $R^{12}$ are defined as in claim 1.

5. The switch element according to claim 2, wherein the compounds according to formula (II) are compounds of at least one of formulas (II-1) to (II-3)

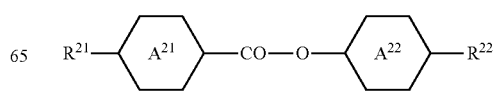
formula (II-1)

-continued formula (II-2)

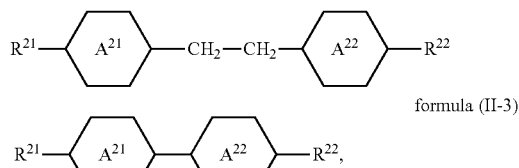

formula (II-3)

where $R^{21}$, $R^{22}$,

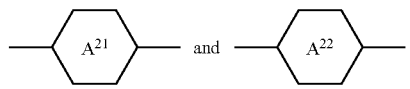

are defined as in claim 2, with the proviso that for formula (II-1),

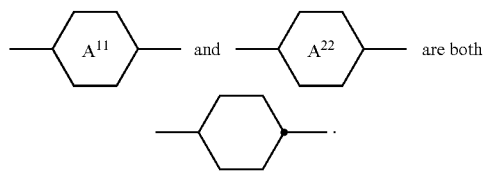

6. The switch element according to claim 3, wherein the compounds according to formula (III) are compounds of at least one of formulas (III-1) to (III-3)

formula (III-1)

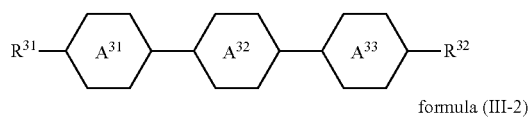

formula (III-2)

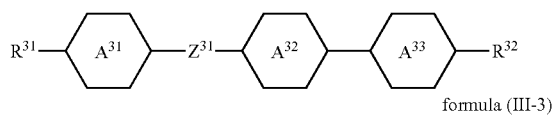

formula (III-3)

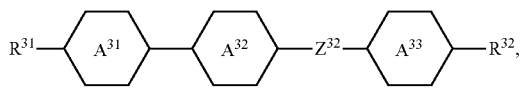

where the groups $R^{31}$, $R^{32}$, $Z^{31}$, $Z^{32}$ and

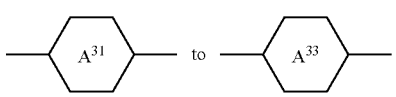

are defined as in claim 3.

7. The switch element according to claim 3, wherein the compounds according to formula (IV) are compounds of at least one of formulas (IV-1) or (IV-2)

formula (IV-1)

formula (IV-2)

where $R^{41}$ and $R^{42}$ and

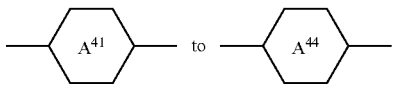

are defined as in claim 3.

8. The switch element according to claim 2, wherein X is on each occurrence, identically or differently, F or Cl.

9. The switch element according to claim 1, having a total concentration of compounds of formula (I) between 5 and 60%.

10. The switch element according to claim 2, having a total concentration of compounds of formulas (I) and (II) between 40 and 100%.

11. The switch element according to claim 1, wherein no electrical wiring, circuitry and/or switching network is present.

12. A method for the regulation of the flow of radiant energy between an interior space and the environment, which comprises regulating the flow with a switch element according to claim 1.

* * * * *